(12) United States Patent
Tomita et al.

(10) Patent No.: US 7,476,859 B2
(45) Date of Patent: Jan. 13, 2009

(54) RADIATION DETECTOR

(75) Inventors: Yasuhiro Tomita, Hamamatsu (JP);
Masanori Kinpara, Hamamatsu (JP);
Michiatsu Nakada, Hamamatsu (JP);
Yuji Shirayanagi, Hamamatsu (JP);
Shinjiro Matsui, Hamamatsu (JP)

(73) Assignee: Hamamatsu Photonics K.K.,
Hamamatsu-shi, Shizuoka (JP)

( * ) Notice: Subject to any disclaimer, the term of this patent is extended or adjusted under 35 U.S.C. 154(b) by 241 days.

(21) Appl. No.: 10/528,232

(22) PCT Filed: Sep. 19, 2003

(86) PCT No.: PCT/JP03/12019

§ 371 (c)(1),
(2), (4) Date: Mar. 18, 2005

(87) PCT Pub. No.: WO2004/027455

PCT Pub. Date: Apr. 1, 2004

(65) Prior Publication Data

US 2005/0288567 A1    Dec. 29, 2005

(30) Foreign Application Priority Data

Sep. 20, 2002    (JP) ............................. 2002-276261

(51) Int. Cl.
*G01J 1/00* (2006.01)
*A61B 6/00* (2006.01)
(52) U.S. Cl. .............................. 250/336.1; 250/363.02; 600/407
(58) Field of Classification Search ................. 600/436, 600/407, 409, 310, 136; 250/370, 484, 366, 250/336.1, 370.01–370.11, 390.01–390.03
See application file for complete search history.

(56) References Cited

U.S. PATENT DOCUMENTS

| | | | |
|---|---|---|---|
| 6,236,880 B1 * | 5/2001 | Raylman et al. | ............ 600/436 |
| 2001/0013576 A1 * | 8/2001 | Miller et al. | ........... 250/363.02 |
| 2004/0061059 A1 * | 4/2004 | Gobel et al. | ........... 250/370.01 |

FOREIGN PATENT DOCUMENTS

| | | |
|---|---|---|
| JP | 10-39027 | 2/1998 |
| JP | 10-039027 | 2/1998 |
| JP | 11-23717 | 1/1999 |
| JP | 2001-305225 | 10/2001 |
| JP | 2002-528729 | 9/2002 |
| WO | WO 02/44755 A2 | 6/2002 |

\* cited by examiner

*Primary Examiner*—Eric F Winakur
*Assistant Examiner*—Lawrence N Laryea
(74) *Attorney, Agent, or Firm*—Drinker Biddle & Reath LLP

(57) ABSTRACT

A sound output portion 7, a power supply switch 4, and a power supply portion 3, which are provided at a detachable portion A of a manipulation grip 1 are configured to be detachable from a main body portion B of the manipulation grip 1. Accordingly, upon sterilization using a sterilizing gas such as an EOG, the sound output portion 7, the power supply switch 4, and the power supply portion 3 can be removed on a detachable portion A basis. This in turn allows for using a sterilizing gas such as EOG to sterilize the radiation detector except the sound output portion 7, the power supply switch 4, and the power supply portion 3, thereby preventing damage caused by a negative pressure in the sound output portion 7.

5 Claims, 25 Drawing Sheets

RADIATION DETECTOR

TECHNICAL FIELD

The present invention relates to radiation detectors with the joint portion of a radiation detector housing which is sealed by means such as an O-ring and a gasket, by welding or by adhesion. More particularly, the invention relates to a radiation detector which is improved to be suitable for sterilization.

BACKGROUND ART

For example, as disclosed in U.S. Pat. No. 6,236,880B1, conventionally known as a radiation detector for detecting radiation is a medical radiation detector equipped with a handheld probe. The radiation detector of this type includes a battery as a power supply and a power supply switch as well as a sound output portion for outputting sound according to the radiation intensity detected.

DISCLOSURE OF THE INVENTION

For a radiation detector of this type for medical use, e.g., a surgical probe used for detecting a metastatic breast cancer nidus using a radiopharmacentical, the probe directly contacts with the patient and may be thus required to be sterilized. In this case, for example, sterilization is performed in general using a sterilizing gas such as ethylene oxide gas (hereinafter referred to as "EOG"). In this sterilization process, a pressure-resistant case accommodating the radiation detector therein is evacuated to a negative pressure so that a sterilizing gas such as EOG is introduced into the pressure-resistant case, thereby allowing the sterilizing gas to pass throughout the entire radiation detector having a negative pressure therein for sterilization.

For general radiation detectors to be sterilized using sterilizing gas such as EOG, the joint portion of the housing is sealed by means such as an O-ring or gasket, by welding, or by adhesion. However, when the radiation detector is actually sterilized using a sterilizing gas such as EOG, the speaker or the like of the sound output portion may be damaged due to the influence of a negative pressure. In this case, the radiation detector may lose the hermeticity of the main body, causing the entire interior of the radiation detector to be exposed to the sterilizing gas such as EOG from the damaged portion. This may result in deterioration or corrosion in various electrodes, or cause damage to the entire radiation detector, to be worse.

Also, consider a case in which a sterilizing gas such as EOG is used to sterilize a radiation detector that employs a mechanically selectable power supply switch for the power supply switch portion. The negative pressure in the radiation detector may cause the sterilizing gas such as EOG to intrude therein through a gap in the power supply switch. In this case, the radiation detector may lose the hermeticity of its main body, causing the entire interior of the radiation detector to be exposed to the sterilizing gas such as EOG. This may result in deterioration or corrosion in various electrodes, or cause damage to the entire radiation detector, to be worse. In addition to this, the gap portions in the power supply switch may be insufficiently sterilized.

Furthermore, some batteries serving as a power supply may not employ a sealed structure. Thus, a radiation detector that should have a sealed structure for the housing joint portion can employ only a limited type of batteries.

Still furthermore, consider such a radiation detector with a button, dial, knob and the like which constitutes a detection sensitivity variable portion capable of varying the detection sensitivity of radiation or a display variable portion capable of varying a sound display or an image display to display the radiation intensity. In this case, during the sterilization using a sterilizing gas such as EOG, the negative pressure may cause the sterilizing gas such as EOG to intrude into the radiation detector through a gap between the button, dial, knob or the like and the main body. In this case, the radiation detector may lose the hermeticity of its main body, causing the entire interior of the radiation detector to be exposed to the sterilizing gas such as EOG. This may result in deterioration or corrosion in various electrodes, or cause damage to the entire radiation detector, to be worse. In addition to this, the gap portions between the button, dial, knob or the like and the main body may be insufficiently sterilized.

It is therefore an object of the present invention to provide a radiation detector which can prevent the negative pressure from causing damage to the hermeticity of the radiation detector main body upon sterilization using a sterilizing gas such as EOG.

A radiation detector according to the present invention has a main body which includes a radiation detecting portion for detecting a radiation intensity and a sound output portion for outputting a sound according to a radiation intensity detected by the radiation detecting portion. The main body also includes a power supply portion for supplying power at least to the radiation detecting portion and the sound output portion. The main body characterized in that the sound output portion is configured to be detachable from the main body.

The radiation detector makes it possible to remove the sound output portion from the main body and thereby use a sterilizing gas such as EOG to sterilize only the main body and the radiation detecting portion excluding the sound output portion. It is thus possible to prevent the negative pressure from causing damage to the sound output portion. This allows for preventing damage to the hermeticity of the radiation detector main body.

Furthermore, a radiation detector according to the present invention has a main body which includes a radiation detecting portion for detecting a radiation intensity, a power supply portion for supplying power at least to the radiation detecting portion, and a power supply switch portion for turning on/off the power supply portion. The radiation detector is characterized in that the power supply switch portion is configured to be detachable from the main body.

The radiation detector makes it possible to remove the power supply switch portion from the main body and thereby use a sterilizing gas such as EOG to sterilize only the main body and the radiation detecting portion excluding the power supply switch portion. In this case, the power supply switch portion does not need to be sealed, thereby making it possible to employ a mechanically selectable switch such as a dipswitch.

Furthermore, a radiation detector according to the present invention has a main body which includes a radiation detecting portion for detecting a radiation intensity. The main body further includes an integrated component having integrally a power supply portion including a battery for supplying power at least to the radiation detecting portion and a power supply switch portion for turning on/off the power supply portion. The radiation detector is characterized in that the integrated component is configured to be detachable from the main body.

The radiation detector makes it possible to remove the integrated component of the power supply portion and the power supply switch portion from the main body. It is thus possible to use a sterilizing gas such as EOG to sterilize only the main body and the radiation detecting portion excluding the integrated component of the power supply portion and the power supply switch portion. In this case, the power supply switch portion does not need to be sealed, thereby making it possible to employ a mechanically selectable switch such as a dipswitch. Additionally, since the power supply portion does not need to be sealed, it is also possible to use a nickel hydride battery which is prohibited from use under a hermetically sealed condition. Moreover, since the battery can be readily replaced, it is possible to use the radiation detector for a long period of time without replacing it.

Furthermore, a radiation detector according to the present invention has a main body which includes a radiation detecting portion for detecting a radiation intensity and a detection sensitivity variable portion for varying a detection sensitivity of the radiation detecting portion. The main body also includes a display variable portion for varying at least one of a sound display and an image display of a radiation intensity detected by the radiation detecting portion. The radiation detector is characterized in that the detection sensitivity variable portion and the display variable portion are configured to be detachable from the main body.

The radiation detector makes it possible to remove the detection sensitivity variable portion and the display variable portion from the main body. It is thus possible to use a sterilizing gas such as EOG to sterilize only the main body and the radiation detecting portion excluding the detection sensitivity variable portion and the display variable portion. In this case, the detection sensitivity variable portion and the display variable portion does not need to be sealed, thereby making it possible to employ an ordinary button, dial, knob or the like as a component of the detection sensitivity variable portion and the display variable portion.

In the arrangements, the sound output portion, the power supply switch portion, the integrated component of the power supply portion and the power supply switch portion, or the detection sensitivity variable portion and the display variable portion may include a connection connector to be detachably connected to a connection connector of the main body. This arrangement allows these portions to be configured to be detachable from the main body via the connection connector. Furthermore, the sound output portion, the power supply switch portion, the integrated component of the power supply portion and the power supply switch portion, or the detection sensitivity variable portion and the display variable portion may be detachably screwed to the main body. Still furthermore, the sound output portion, the power supply switch portion, the integrated component of the power supply portion and the power supply switch portion, or the detection sensitivity variable portion and the display variable portion may include an engagement portion to detachably engage an engagement portion of the main body. This arrangement allows these portions to be configured to be detachable from the main body via the engagement portion.

BEST MODE FOR CARRYING OUT THE INVENTION

Figure 1:
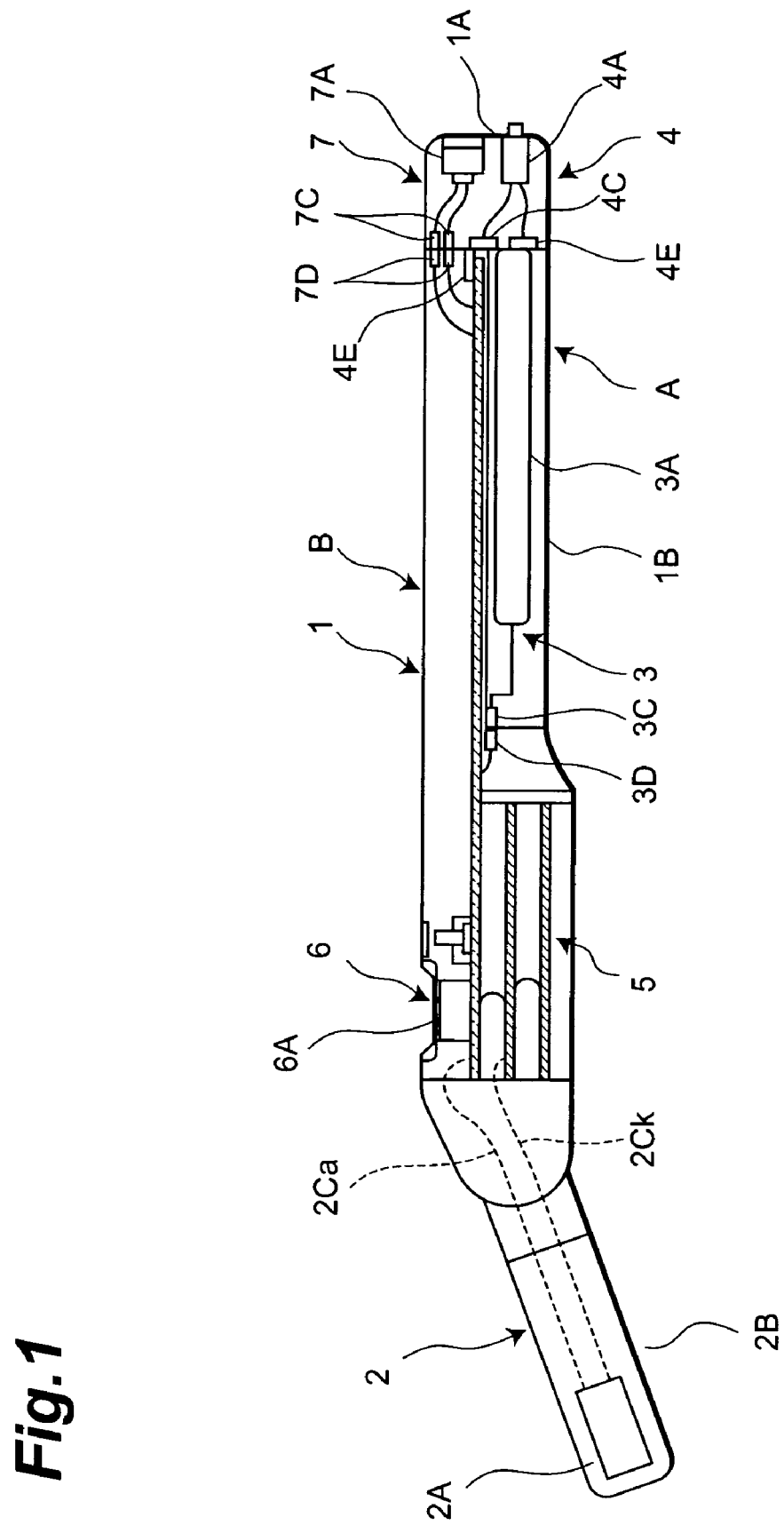
FIG. 1 is a longitudinal sectional view illustrating a schematic structure of a radiation detector according to a first embodiment of the present invention.

Now, a radiation detector according to the present invention will be explained below with reference to the accompanying drawings in accordance with the embodiments. In the drawings to be referred to, FIG. 1 is a longitudinal sectional view illustrating a schematic structure of a radiation detector according to a first embodiment of the present invention, and FIG. 2 is an explanatory view illustrating the operation of the radiation detector shown in FIG. 1.

Figure 2:
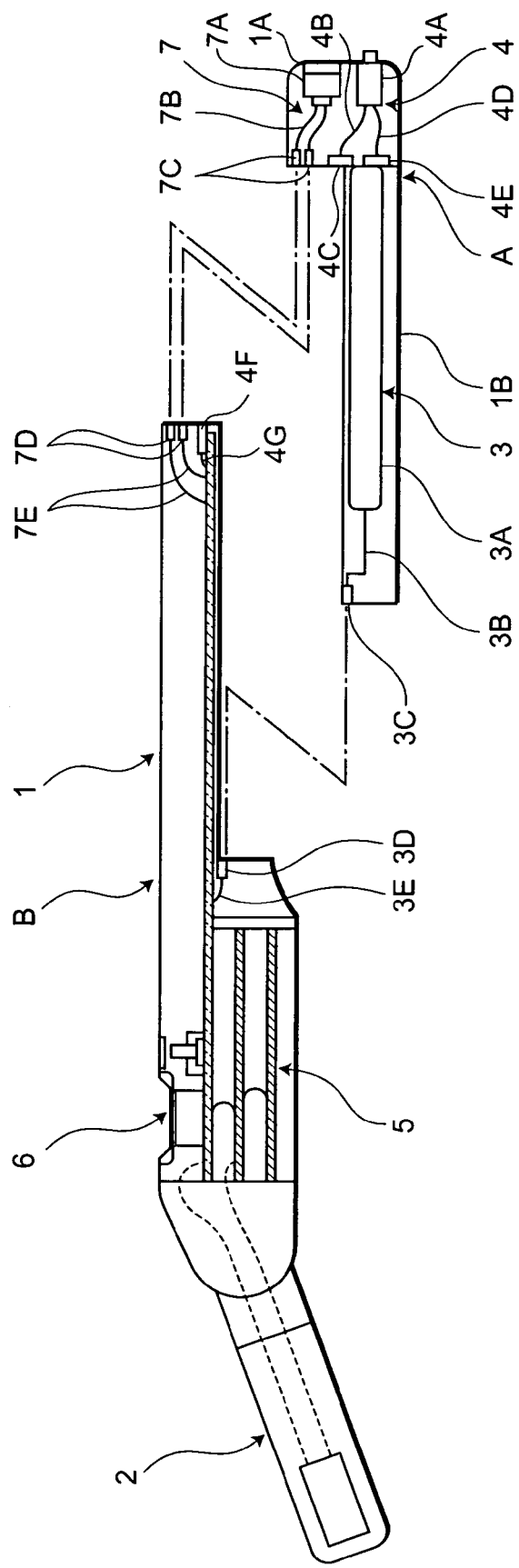
FIG. 2 is an exploded view illustrating the operation of the radiation detector shown in FIG. 1.

As shown in FIG. 1, a radiation detector according to a first embodiment includes a manipulation grip 1 which is handheld for manipulation as a main body. The radiation detector is configured as a handheld cordless surgical probe in which a radiation detecting probe 2 serving as a radiation detecting portion protrudes from the distal end of the manipulation grip 1. For example, this radiation detector is employed for detecting a metastatic breast cancer nidus using a radiopharmaceutical.

Inside the manipulation grip 1 which is made hollow, this radiation detector includes a power supply portion 3, a power supply switch portion 4, a control portion 5, a liquid crystal display portion 6, and a sound output portion 7. In this arrangement, most part of the control portion 5 and the liquid crystal display portion 6 are disposed within the distal end portion of the manipulation grip 1, while a liquid crystal panel 6A of the liquid crystal display portion 6 is disposed on the circumferential surface at the distal end portion of the manipulation grip 1. Additionally, the sound output portion 7 and the power supply switch portion 4 are disposed at an upper and lower position in the proximal end portion of the manipulation grip 1. The power supply portion 3 is disposed at a lower portion of the manipulation grip 1 in front of the power supply switch portion 4.

The radiation detecting probe 2 is configured as a hermetic probe in which a radiation detecting element 2A for detecting a radiation intensity is hermetically built in a cap-shaped probe cover 2B. The radiation detecting element 2A is a semiconductor element which generates a voltage pulse having a pulse height value corresponding to the energy of the radiation photon, and electrically connected to the control portion 5 of the manipulation grip 1 side via a lead wire 2C.

The power supply portion 3 includes a battery 3A as a power supply. When the power supply switch portion 4 is turned on, the power supply portion 3 is designed to supply power to the radiation detecting probe 2, the liquid crystal display portion 6, and the sound output portion 7 via the control portion 5.

Although not illustrated, the control portion 5 includes a power supply circuit, a signal processing circuit, and a drive circuit, and receives a detection pulse signal which is output according to the radiation intensity by the radiation detecting element 2A of the radiation detecting probe 2. The control portion 5 performs a pulse height discrimination on the detection pulse signal based on a predetermined threshold value to output an input pulse signal, which is in turn processed in the signal processing circuit. The control portion 5 then outputs respective drive signals individually to the liquid crystal display portion 6 and the sound output portion 7 according to an increase or decrease in the number of input pulses. That is, the control portion 5 delivers a liquid crystal drive signal to the liquid crystal display portion 6 according to an increase or decrease in the number of input pulses. On the other hand, the control portion 5 delivers a speaker drive signal such as a frequency modulated sound or a beep to the sound output portion 7 according to an increase or decrease in the number of input pulses.

In accordance with the liquid crystal drive signal from the control portion 5, the liquid crystal display portion 6 displays, on the liquid crystal panel 6A, the data on the radiation intensity detected by the radiation detecting element 2A. On the other hand, in accordance with the speaker drive signal from the control portion 5, the sound output portion 7 allows a speaker 7A to give off the frequency modulated sound or the beep indicative of the radiation intensity detected by the radiation detecting element 2A.

In this arrangement, with the radiation detector according to the first embodiment, an integrated component of the sound output portion 7, the power supply switch portion 4, and the power supply portion 3 is configured to be detachable from the manipulation grip 1 serving as the main body. To this end, as shown in FIG. 2, the manipulation grip 1 is configured to be divided into a detachable portion A and the other main body portion B. The detachable portion A is configured to be a separate case with no opening, which integrally includes a grip end portion 1A for accommodating the sound output portion 7 and the power supply switch portion 4 and a lower grip body portion 1B for accommodating the power supply portion 3. The main body portion B is also configured as a separate case with no opening.

To make the detachable portion A detachable from the main body portion B of the manipulation grip 1, a power supply portion connection connector 3C connected to the battery 3A via a lead wire 3B is provided on the tip face of the lower grip body portion 1B in the detachable portion A. Additionally, on the front end face of the grip end portion 1A in the detachable portion A, provided is a pair of speaker connection connectors 7C connected to the speaker 7A via lead wires 7B. Also provided is one switch connection connector 4C connected to one terminal of a power supply switch 4A of the power supply switch portion 4 via lead wires 7B.

In this arrangement, the other switch connection connector 4E connected to the other terminal of the power supply switch 4A via a lead wire 4D is directly connected to the electrode of the battery 3A of the power supply portion 3.

On the other hand, in the main body portion B of the manipulation grip 1, consider a face that is joined to the tip face of the lower grip body portion 1B in the detachable portion A. On this face, there is provided a power supply portion connection connector 3D to which the power supply portion connection connector 3C on the detachable portion A side is detachably connected. Also consider a face that is joined to the front end face of the grip end portion 1A in the detachable portion A. On this face, there are provided speaker connection connectors 7D and a switch connection connector 4F to which the speaker connection connectors 7C and the one switch connection connector 4C on the detachable portion A side are detachably connected, respectively. These power supply portion connection connector 3D, the speaker connection connectors 7D, and the switch connection connector 4F are connected to the control portion 5 via lead wires 3E, 7E, and 4G, respectively.

In this arrangement, the power supply portion connection connector 3C on the detachable portion A side is designed to be positively attached to or detached from the power supply portion connection connector 3D on the main body portion B side such that the pin and the socket click into place. Additionally, the speaker connection connectors 7C on the detachable portion A side is designed to be positively attached to or detached from the speaker connection connectors 7D on the main body portion B side such that the pin and the socket click into place. Likewise, the switch connection connector 4C on the detachable portion A side is designed to be positively attached to or detached from the switch connection connector 4F on the main body portion B side such that the pin and the socket click into place. In this connection condition, the detachable portion A is integrated with the main body portion B of the manipulation grip 1 (refer to FIG. 1).

The radiation detector of the first embodiment configured as described above is used, for example, for detecting a metastatic breast cancer nidus using a radiopharmaceutical. In this application, when the distal end of the radiation detecting probe 2 is directed to the measured portion of a patient, the radiation coming from the measured portion will be made incident upon the radiation detecting element 2A. This causes the radiation detecting element 2A to output a detection pulse signal associated with the radiation intensity made incident thereon to the control portion 5 on the manipulation grip 1 side.

When the number of input pulses has exceeded a predetermined threshold value at which the speaker 7A is driven, the control portion 5 having received detection pulse signals from the radiation detecting element 2A outputs a speaker drive signal to the speaker 7A to give off a frequency modulated sound or a beep. Likewise, the control portion 5 outputs a liquid crystal drive signal to the liquid crystal display portion 6, causing the liquid crystal panel 6A to display data associated with the radiation intensity.

Here, the radiation detector according to the first embodiment is sterilized using sterilizing gas such as EOG prior to its use because the radiation detector is used for detecting a metastatic breast cancer nidus using a radiopharmacentical or the like. In this sterilization process, a pressure-resistant case accommodating the radiation detector therein is evacuated to a negative pressure so that a sterilizing gas such as EOG is introduced into the pressure-resistant case, thereby allowing the sterilizing gas to pass throughout the entire radiation detector having a negative pressure therein for sterilization.

For this purpose, in the radiation detector according to the first embodiment, the detachable portion A having integrally the grip end portion 1A and the lower grip body portion 1B is removed from the main body portion B of the manipulation grip 1. Then, the sterilizing gas such as EOG is used to sterilize only on the main body portion B of the manipulation grip 1 and the radiation detecting probe 2 excluding the sound output portion 7, the power supply switch portion 4, and the power supply portion 3.

In this manner, the radiation detector according to the first embodiment makes it possible to perform sterilization using a sterilizing gas such as EOG with the sound output portion 7, the power supply switch portion 4, and the power supply portion 3 being removed in the manipulation grip 1 on a detachable portion A basis. This makes it possible to prevent damage to the speaker 7A of the sound output portion 7 caused by a negative pressure in the pressure-resistant case.

Furthermore, since the power supply switch portion 4 dose not need to be sealed, it is possible to employ as the power supply switch 4A a mechanically selectable switch such as a dipswitch.

Still furthermore, the power supply portion 3 does not need to be sealed, it is also possible to use as a battery 3A a nickel hydride battery which is prohibited from use under a hermetically sealed condition. Moreover, since the power supply portion 3 including the battery 3A can be replaced on a detachable portion A basis, it is possible to use the radiation detector for a long period of time without replacing the entirety thereof.

Now, the radiation detectors according to the present invention will be described in sequence in accordance with the other embodiments. These embodiments are based on the first embodiment shown in FIG. 1 and FIG. 2, and identical components indicated by identical symbols will not be explained in detail.

Figure 3:
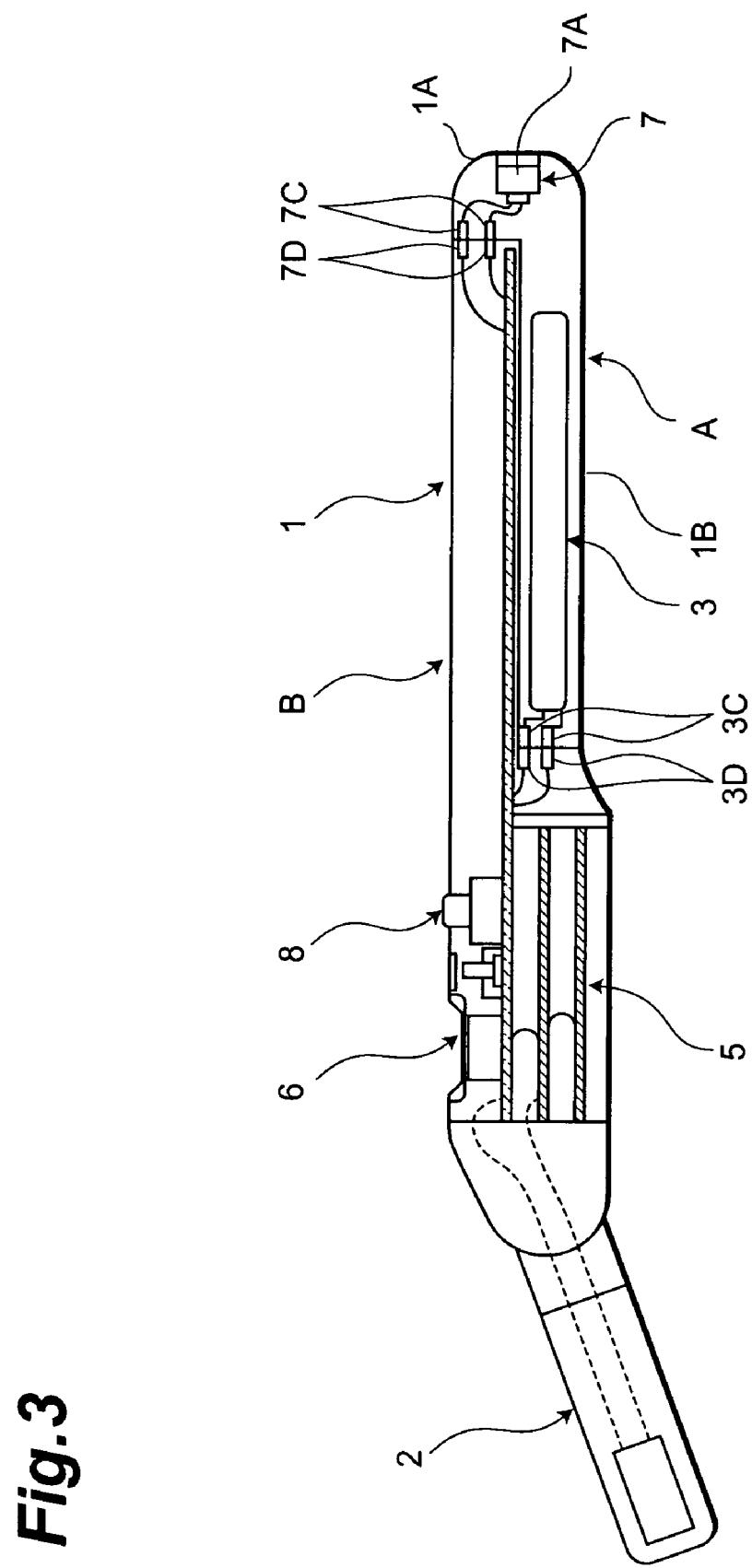
FIG. 3 is a longitudinal sectional view illustrating a schematic structure of a radiation detector according to a second embodiment of the present invention.
Figure 4:
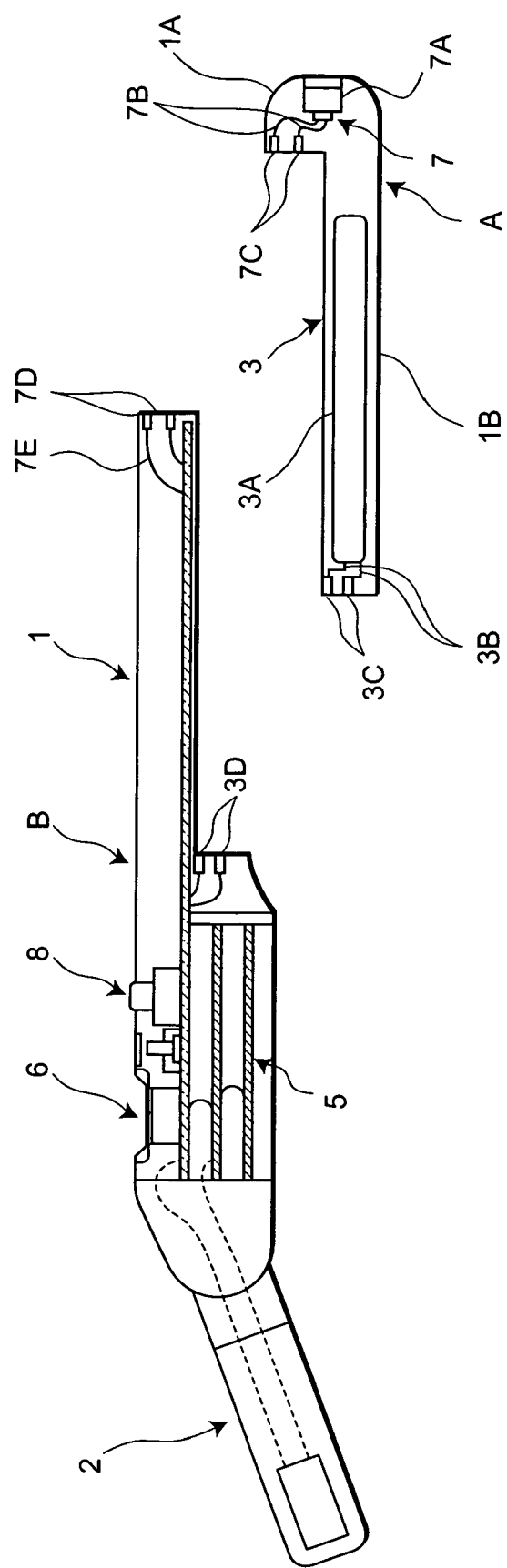
FIG. 4 is an exploded view illustrating the operation of the radiation detector shown in FIG. 3.

A radiation detector according to a second embodiment is configured such that the integrated component of the sound output portion 7 and the power supply portion 3 is detachable from the manipulation grip 1 as the main body. As shown in FIG. 3 and FIG. 4, this radiation detector employs a power supply switch portion 8, which is a substitute for the power supply switch portion 4 (refer to FIG. 2) provided in the grip end portion 1A on the detachable portion A side of the manipulation grip 1 in the radiation detector of the first embodiment (refer to FIG. 1 and FIG. 2). The power supply switch portion 8 is provided behind the liquid crystal display portion 6 in the main body portion B of the manipulation grip 1. In this arrangement, on the tip face of the lower grip body portion 1B in the detachable portion A, provided is a pair of power supply portion connection connectors 3C which are connected to the battery 3A via a pair of lead wires 3B.

Accordingly, in the main body portion B of the manipulation grip 1, consider a face that is joined to the tip face of the lower grip body portion 1B in the detachable portion A. On this face, there are provided a pair of power supply portion connection connectors 3D to which the pair of power supply portion connection connectors 3C on the detachable portion A side are detachably connected. The pair of power supply portion connection connectors 3D are connected to the control portion 5 via the power supply switch portion 8.

In the radiation detector according to the second embodiment, the pair of power supply portion connection connectors 3C on the detachable portion A side are connected to the pair of power supply portion connection connectors 3D on the main body portion B side. Additionally, the pair of speaker connection connectors 7C on the detachable portion A side are connected to the pair of speaker connection connectors 7D on the main body portion B side. This arrangement allows the detachable portion A to be integrated with the main body portion B of the manipulation grip 1 (refer to FIG. 3).

According to the radiation detector of the second embodiment, it is possible to perform sterilization using a sterilizing gas such as EOG with the sound output portion 7 and the power supply portion 3 being removed in the manipulation grip 1 on a detachable portion A basis. This makes it possible to prevent damage to the speaker 7A of the sound output portion 7 caused by a negative pressure in the pressure-resistant case. Furthermore, since the power supply portion 3 does not need to be sealed, it is possible to use as a battery 3A a nickel hydride battery which is prohibited from use under a hermetically sealed condition. Moreover, since the power supply portion 3 including the battery 3A can be replaced on a detachable portion A basis, it is possible to use the radiation detector for a long period of time without replacing the entirety thereof.

Figure 5:
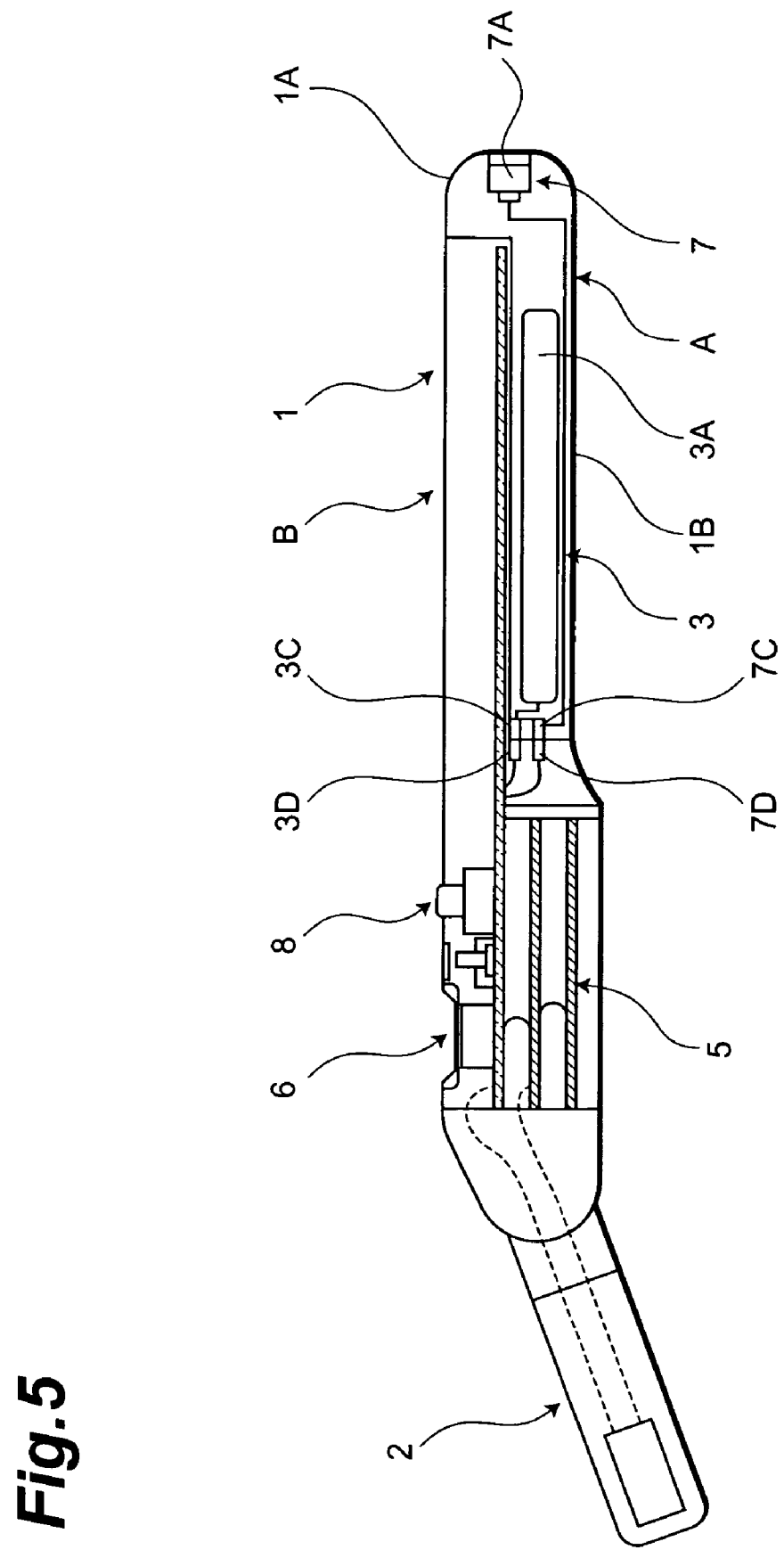
FIG. 5 is a longitudinal sectional view illustrating a schematic structure of a radiation detector according to a third embodiment of the present invention.
Figure 6:
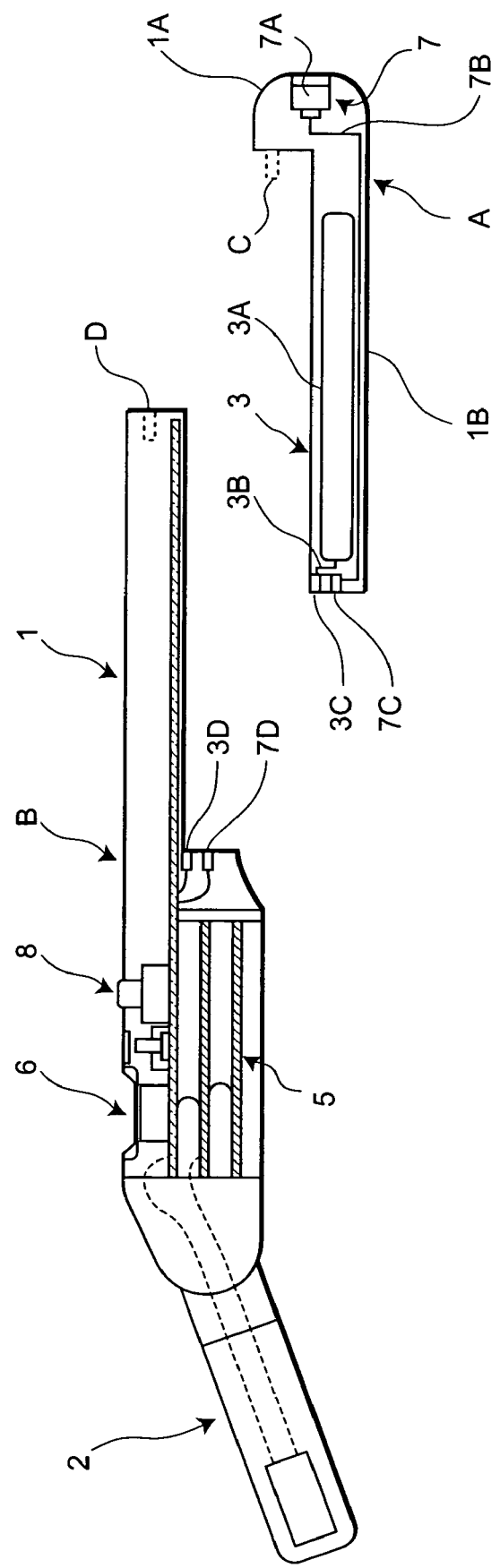
FIG. 6 is an exploded view illustrating the operation of the radiation detector shown in FIG. 5.

A radiation detector according to a third embodiment is configured such that the integrated component of the sound output portion 7 and the power supply portion 3 is detachable from the manipulation grip 1 as the main body. As shown in FIG. 5 and FIG. 6, in this radiation detector, the pair of speaker connection connectors 7C on the detachable portion A side in the radiation detector of the second embodiment (refer to FIG. 3 and FIG. 4) are placed side by side on the tip face of the lower grip body portion 1B in the detachable portion A. Additionally, the pair of power supply portion connection connectors 3C that are provided on the tip face of the lower grip body portion 1B are placed side by side. Accordingly, the radiation detector of the third embodiment includes the pair of speaker connection connectors 7D on the main body portion B side in the radiation detector of the second embodiment. The speaker connection connectors 7D are placed side by side on a face that is joined to the tip face of the lower grip body portion 1B in the detachable portion A of the main body portion B. Furthermore, the pair of power supply portion connection connectors 3D which are provided on this joint face are also placed side by side.

In the radiation detector according to the third embodiment, the pair of power supply portion connection connectors 3C on the detachable portion A side are connected to the pair of power supply portion connection connectors 3D on the main body portion B side. Additionally, the pair of speaker connection connectors 7C on the detachable portion A side are connected to the pair of speaker connection connectors 7D on the main body portion B side. This arrangement allows the detachable portion A to be integrated with the main body portion B of the manipulation grip 1 (refer to FIG. 5)

In the radiation detector according to the third embodiment, to ensure the mounting state the detachable portion A to the main body portion B, for example, it is preferable to provide a recessed and projected engagement portion made up of engagement pins "C" and engagement holes "D" between the front end face of the grip end portion 1A in the detachable portion A and the joint face of the main body portion B that is jointed thereto. Alternatively, a groove fitting portion such as a dovetail groove may be provided between the upper surface of the lower grip body portion 1B in the detachable portion A and the joint face of the main body portion B that is jointed thereto.

According to the radiation detector of the third embodiment, it is possible to perform sterilization using a sterilizing gas such as EOG with the sound output portion 7 and the power supply portion 3 being removed in the manipulation grip 1 on a detachable portion A basis. This makes it possible to prevent damage to the speaker 7A of the sound output portion 7 caused by a negative pressure in the pressure-resistant case. Furthermore, since the power supply portion 3 does not need to be sealed, it is possible to use as the battery 3A a nickel hydride battery which is prohibited from use under a hermetically sealed condition. Moreover, since the power supply portion 3 including a battery 3A can be replaced on a detachable portion A basis, it is possible to use the radiation detector for a long period of time without replacing the entirety thereof.

Figure 7:
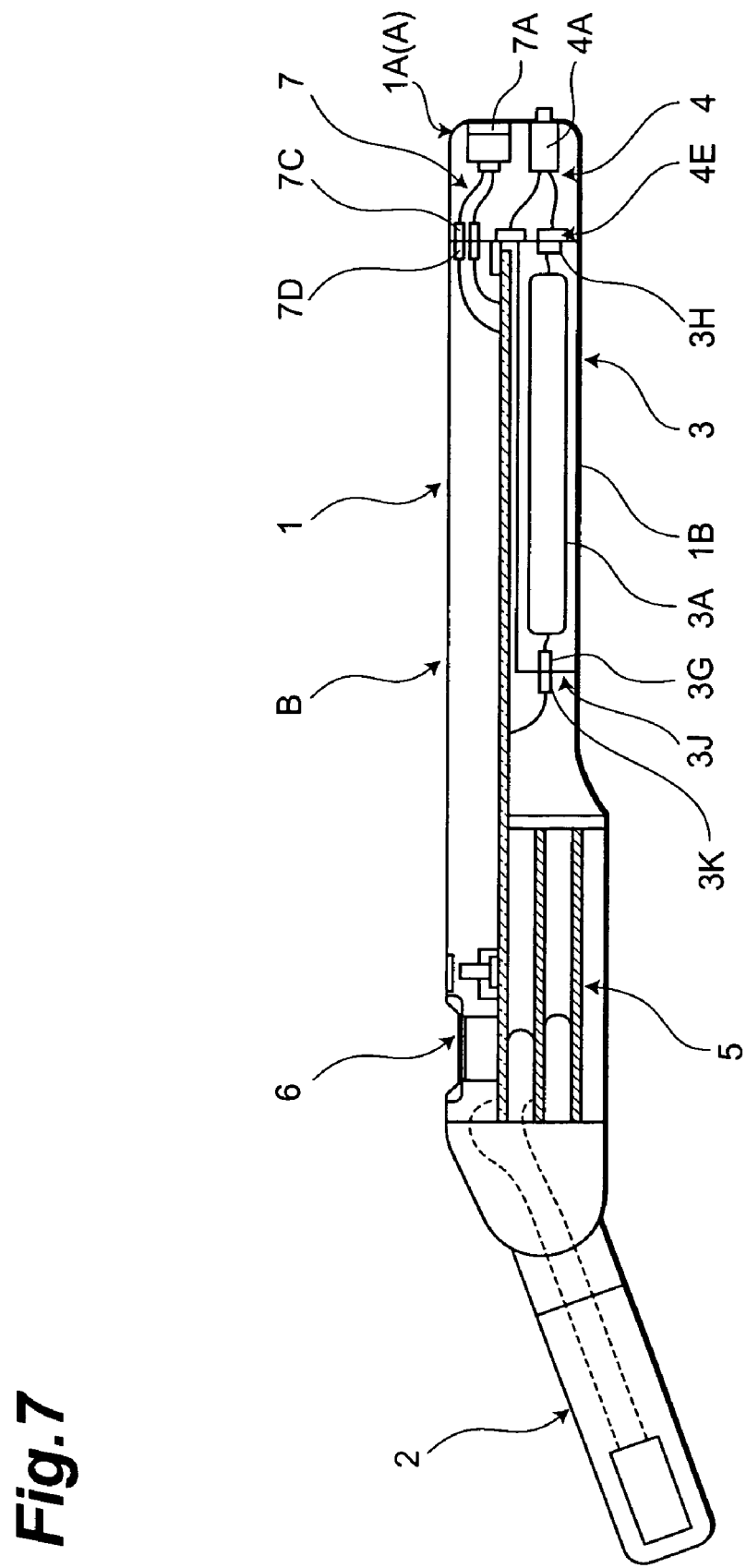
FIG. 7 is a longitudinal sectional view illustrating a schematic structure of a radiation detector according to a fourth embodiment of the present invention.
Figure 8:
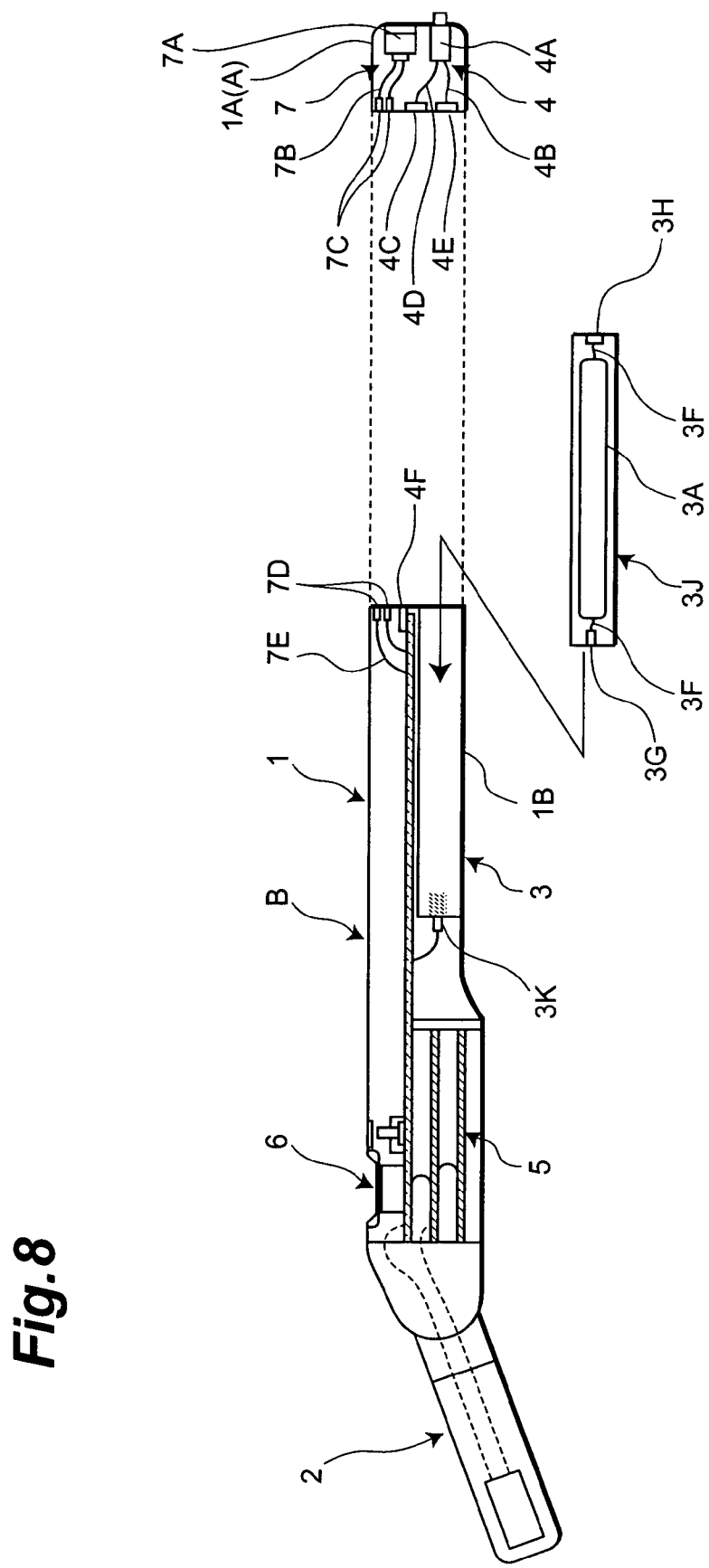
FIG. 8 is an exploded view illustrating the operation of the radiation detector shown in FIG. 7.

A radiation detector according to a fourth embodiment is configured such that the integrated component of the sound output portion 7 and the power supply switch portion 4 as well as a battery portion 3J are detachable from the manipulation grip 1 as the main body. As shown in FIG. 7 and FIG. 8, this radiation detector allows the detachable portion A (refer to FIG. 2) according to the radiation detector of the first embodiment (refer to FIG. 1 and FIG. 2) to include only the grip end portion 1A. The lower grip body portion 1B is integrated with the main body portion B of the manipulation grip 1, with the power supply portion 3 provided in the lower grip body portion 1B on the main body portion B side.

The power supply portion 3 includes the battery portion 3J in which battery connection connectors 3G and 3H are connected in advance to both the electrodes of the battery 3A via lead wires 3F and 3F. The battery portion 3J is configured such that one battery connection connector 3G is detachably connected to a power supply portion connection connector 3K, which is provided in the lower grip body portion 1B on the main body portion B side. Additionally, the other switch connection connector 4E on the detachable portion A side is detachably connected to the other battery connection connector 3H.

In the radiation detector according to the fourth embodiment, the pair of speaker connection connectors 7C on the detachable portion A side are connected to the pair of speaker connection connectors 7D on the main body portion B side. Additionally, the one switch connection connector 4C on the detachable portion A side is connected to the one switch connection connector 4F on the main body portion B side. Furthermore, the other switch connection connector 4E is detachably connected to the battery connection connector 3H of the battery portion 3J. This arrangement allows the detachable portion A to be integrated with the main body portion B of the manipulation grip 1 (refer to FIG. 7).

The radiation detector according to the fourth embodiment also allows sterilization to be performed using a sterilizing gas such as EOG, in a state where the sound output portion 7 and the power supply switch portion 4 in the manipulation grip 1 is removed on a detachable portion A basis, and the battery portion 3J is also removed from the main body portion B of the manipulation grip 1. This makes it possible to prevent damage to the speaker 7A of the sound output portion 7 caused by a negative pressure in the pressure-resistant case.

Furthermore, since the power supply switch portion 4 does not need to be sealed, it is possible to employ as the power supply switch 4A a mechanically selectable switch such as a dipswitch. Still furthermore, since the battery portion 3J is detachable, it is also possible to use as a battery 3A a nickel hydride battery which is prohibited from use under a hermetically sealed condition. Moreover, the battery portion 3J can be replaced, thereby making it possible to use the radiation detector for a long period of time without replacing the entirety thereof.

Figure 9:
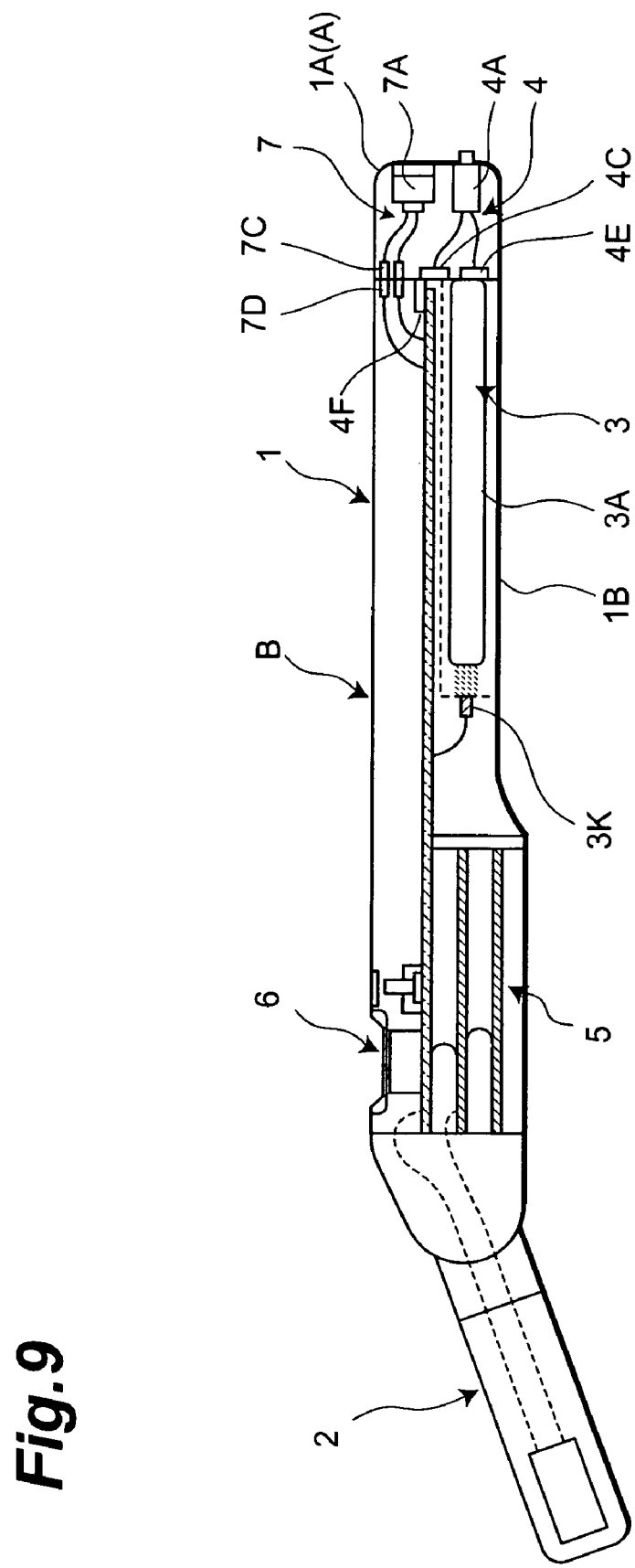
FIG. 9 is a longitudinal sectional view illustrating a schematic structure of a radiation detector according to a fifth embodiment of the present invention.
Figure 10:
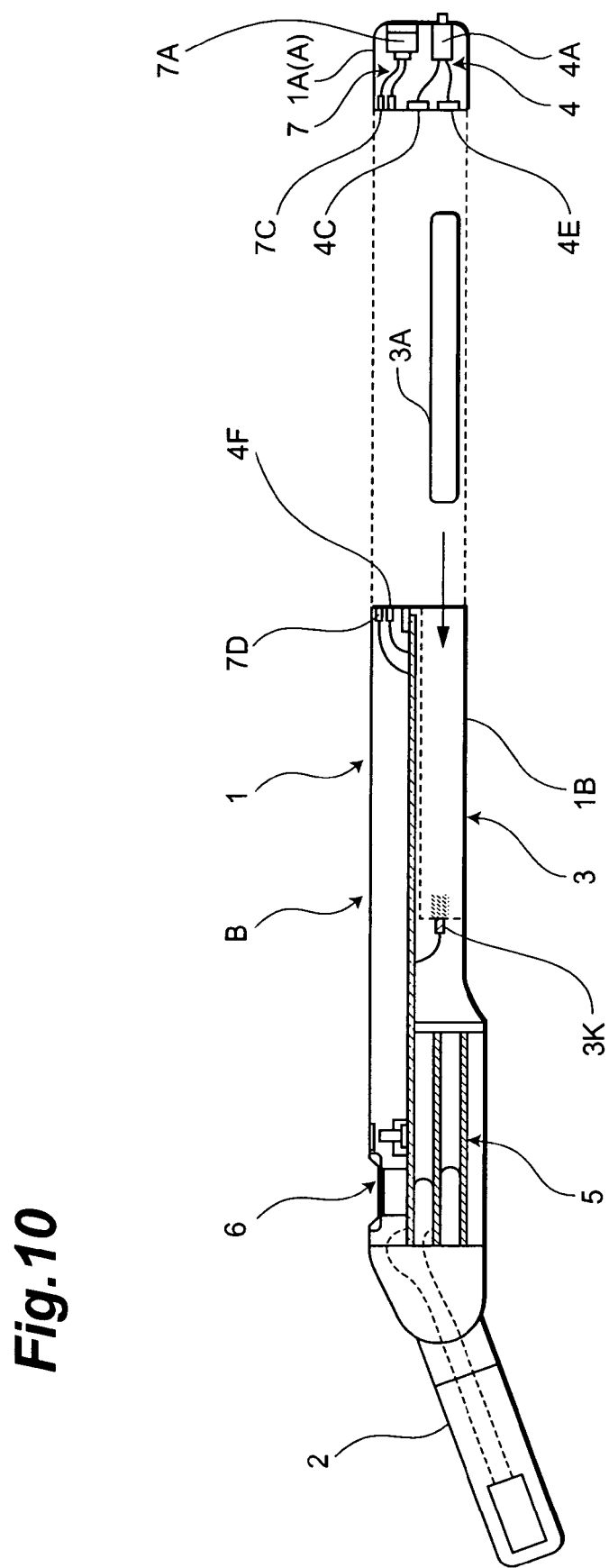
FIG. 10 is an exploded view illustrating the operation of the radiation detector shown in FIG. 9.

A radiation detector according to a fifth embodiment is configured such that the integrated component of the sound output portion 7 and the power supply switch portion 4 as well as the battery 3A are detachable from the manipulation grip 1 as the main body. As shown in FIG. 9 and FIG. 10, this radiation detector allows only the battery 3A to be replaceable instead of the battery portion 3J in the radiation detector of the fourth embodiment (refer to FIG. 7 and FIG. 8). One of the electrodes of the battery 3A is connected to the power supply portion connection connector 3K, which is provided in the lower grip body portion 1B on the main body portion B side, while the other electrode is connected to the switch connection connector 4E on the detachable portion A side.

In the radiation detector according to the fifth embodiment, the pair of speaker connection connectors 7C on the detachable portion A side are connected to the pair of speaker connection connectors 7D on the main body portion B side. Additionally, the one switch connection connector 4C on the detachable portion A side is connected to the one switch connection connector 4F on the main body portion B side. Furthermore, the other switch connection connector 4E is connected to the other electrode of the battery 3A. This arrangement allows the detachable portion A to be integrated with the main body portion B of the manipulation grip 1 (refer to FIG. 9).

The radiation detector according to the fourth embodiment also allows sterilization to be performed using a sterilizing gas such as EOG, in a state where the sound output portion 7 and the power supply switch portion 4 in the manipulation grip 1 are removed on a detachable portion A basis, and the battery 3A is also removed from the main body portion B of the manipulation grip 1. This makes it possible to prevent damage to the speaker 7A of the sound output portion 7 caused by a negative pressure in the pressure-resistant case.

Furthermore, since the power supply switch portion 4 needs not to be sealed, it is possible to employ as the power supply switch 4A a mechanically selectable switch such as a dipswitch. Still furthermore, since the battery 3A is detachable, it is also possible to use as a battery 3A a nickel hydride battery which is prohibited from use under a hermetically sealed condition. Moreover, the battery 3A can be replaced, thereby making it possible to use the radiation detector for a long period of time without replacing the entirety thereof.

Figure 11:
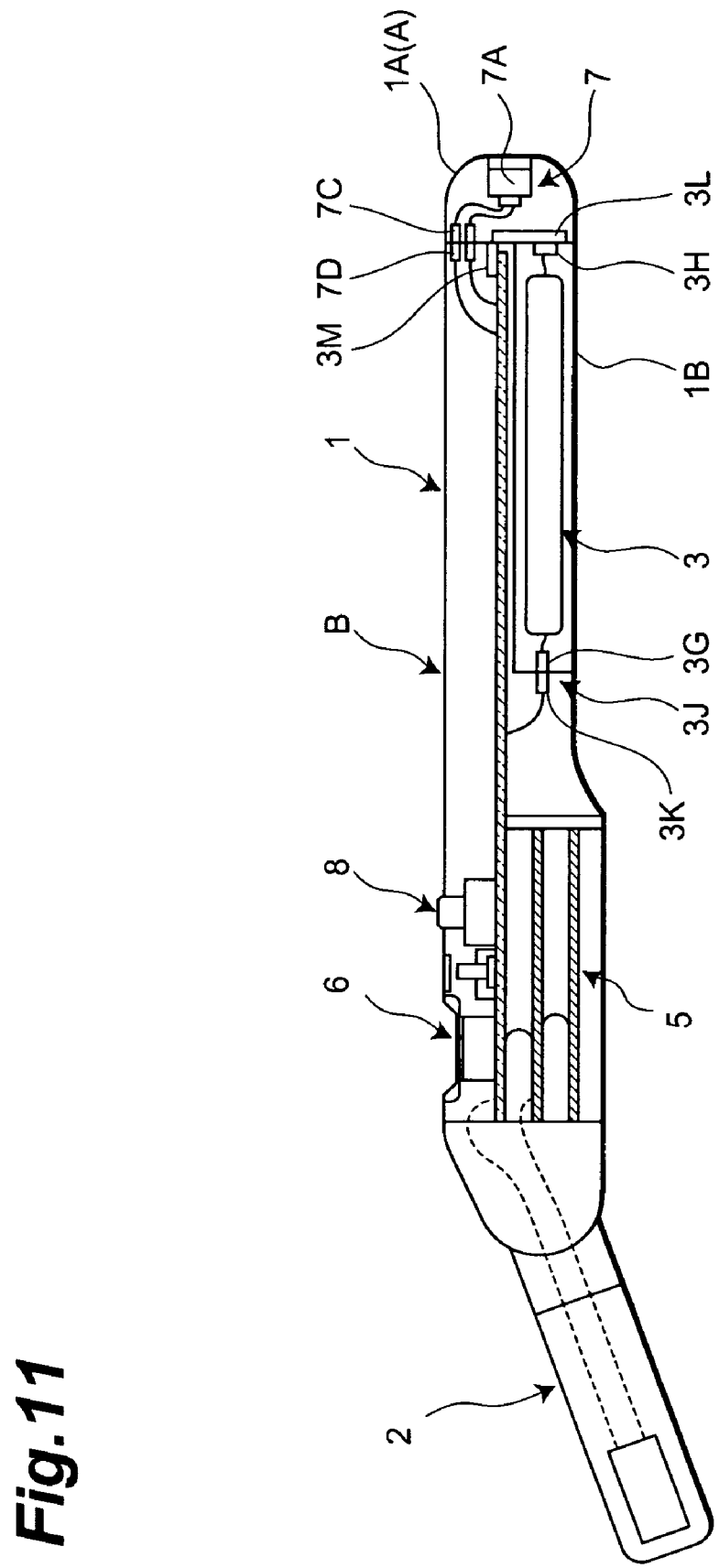
FIG. 11 is a longitudinal sectional view illustrating a schematic structure of a radiation detector according to a sixth embodiment of the present invention.
Figure 12:
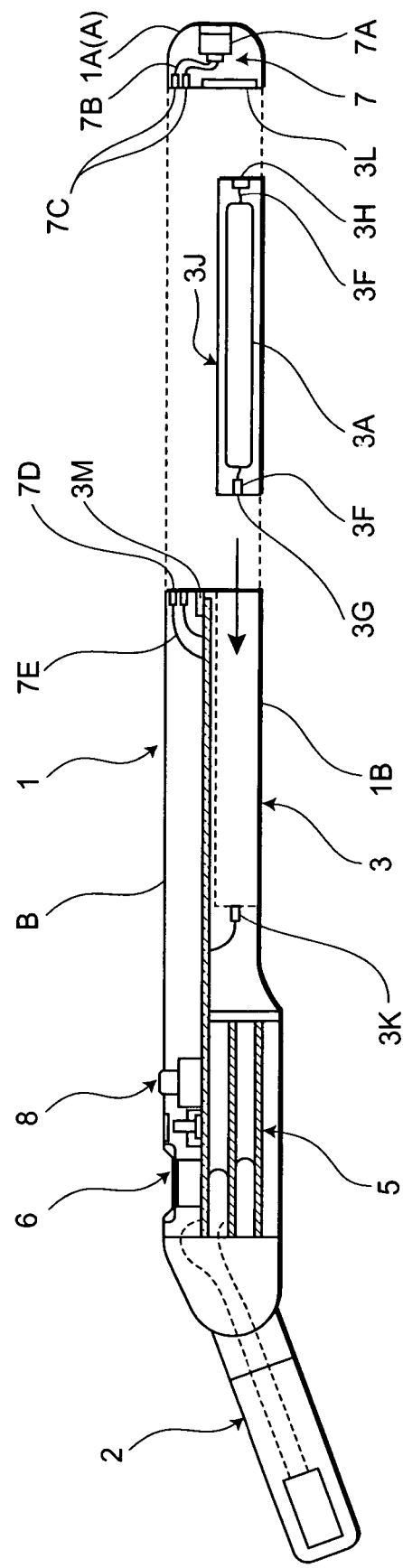
FIG. 12 is an exploded view illustrating the operation of the radiation detector shown in FIG. 11.

A radiation detector according to a sixth embodiment is configured such that the sound output portion 7 and the power supply portion 3 are individually detachable from the manipulation grip 1 as the main body. As shown in FIG. 11 and FIG. 12, this radiation detector employs the power supply switch portion 8. The power supply switch portion 8 is a substitute for the power supply switch portion 4 (refer to FIG. 8) which is provided in the grip end portion 1A on the detachable portion A side of the manipulation grip 1 in the radiation detector of the fourth embodiment (refer to FIG. 7 and FIG. 8). The power supply switch portion 8 is provided behind the liquid crystal display portion 6 in the main body portion B of the manipulation grip 1. In this arrangement, on the front end face of the grip end portion 1A constituting the detachable portion A, provided is a power supply portion connection connector 3L which is detachably connected to the battery connection connector 3H of the battery portion 3J. Accordingly, in the main body portion B of the manipulation grip 1, consider a face that is joined to the front end face of the grip end portion 1A in the detachable portion A. On this face, there is provided a power supply connection terminal 3M which is in contact with the power supply portion connection connector 3L.

In the radiation detector according to the sixth embodiment, the pair of speaker connection connectors 7C on the detachable portion A side are connected to the pair of speaker connection connectors 7D on the main body portion B side. Additionally, the power supply portion connection connector 3L on the detachable portion A side is detachably connected to the battery connection connector 3H of the battery portion 3J. This arrangement allows the detachable portion A to be integrated with the main body portion B of the manipulation grip 1 (refer to FIG. 11).

According to the radiation detector of the sixth embodiment, it is possible to perform sterilization using a sterilizing gas such as EOG, in a state where that the sound output portion 7 is removed in the manipulation grip 1 on a detachable portion A basis, and the battery portion 3J is also removed from the main body portion B of the manipulation grip 1. This makes it possible to prevent damage to the speaker 7A of the sound output portion 7 caused by a negative pressure in the pressure-resistant case.

Furthermore, since the battery portion 3J is detachable, it is also possible to use as a battery 3A a nickel hydride battery which is prohibited from use under a hermetically sealed condition. Moreover, the battery portion 3J can be replaced, thereby making it possible to use the radiation detector for a long period of time without replacing the entirety thereof.

Figure 13:
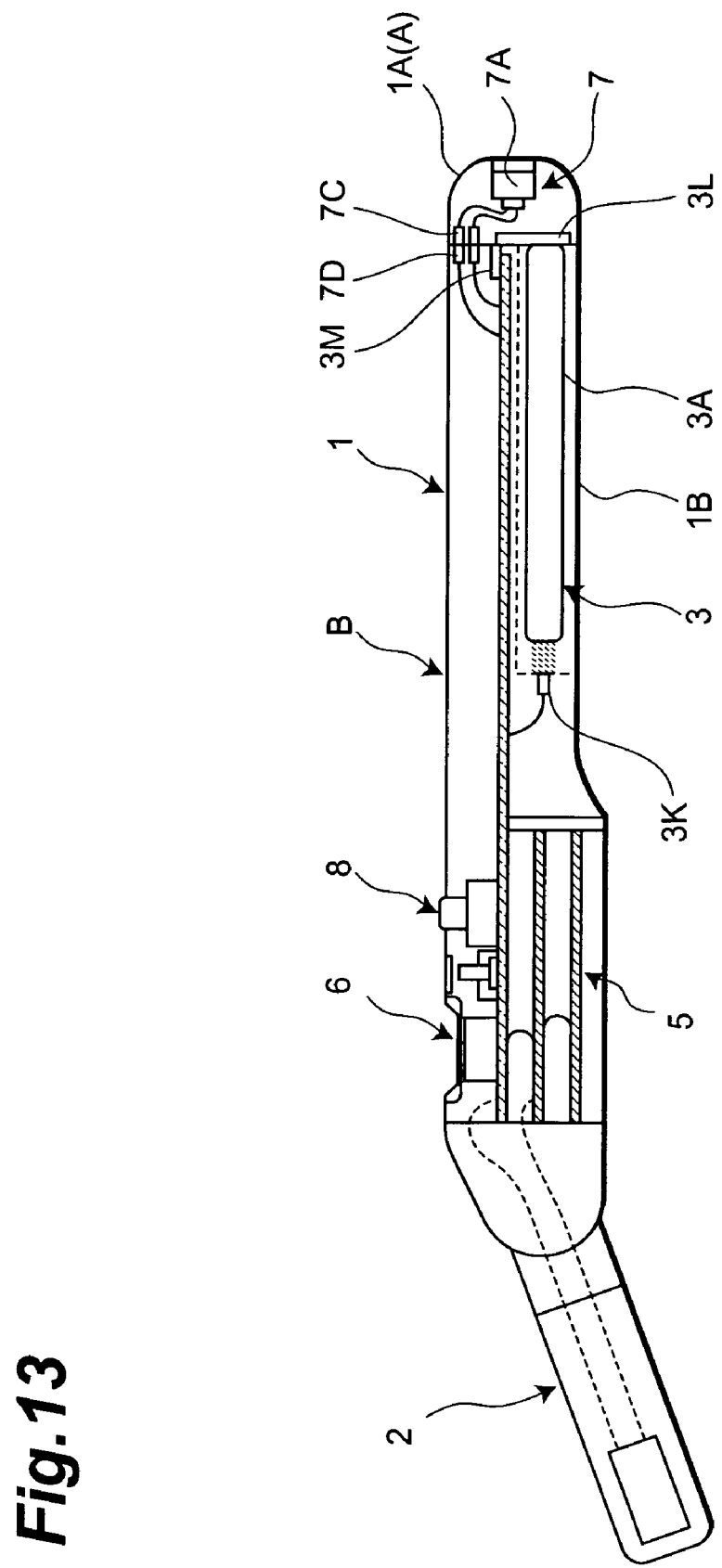
FIG. 13 is a longitudinal sectional view illustrating a schematic structure of a radiation detector according to a seventh embodiment of the present invention.
Figure 14:
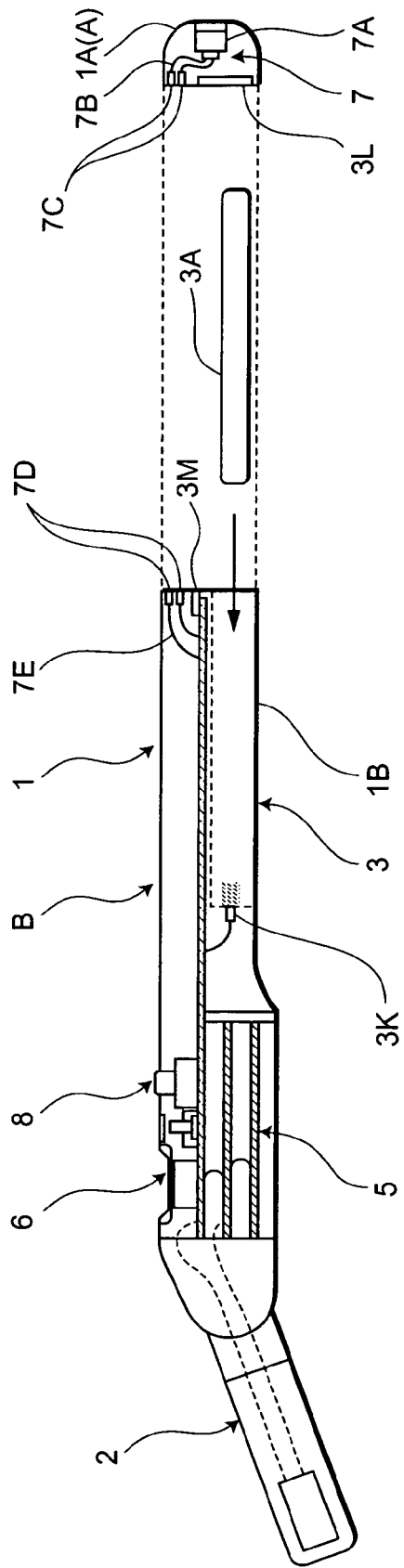
FIG. 14 is an exploded view illustrating the operation of the radiation detector shown in FIG. 13.

A radiation detector according to a seventh embodiment is configured such that the sound output portion 7 and the battery 3A are individually detachable from the manipulation grip 1 as the main body. As shown in FIG. 13 and FIG. 14, this radiation detector allows only the battery 3A to be replaceable instead of the battery portion 3J in the radiation detector of the sixth embodiment (refer to FIG. 11 and FIG. 12). One of the electrodes of the battery 3A is connected to the power supply portion connection connector 3K, which is provided in the lower grip body portion 1B on the main body portion B side, while the other electrode is detachably connected to the power supply portion connection connector 3L on the detachable portion A side.

The radiation detector according to the seventh embodiment also allows sterilization to be performed using a sterilizing gas such as EOG, in a state where that the sound output portion 7 in the manipulation grip 1 is removed on a detachable portion A basis, and the battery 3A is also removed from the main body portion B of the manipulation grip 1. This makes it possible to prevent damage to the speaker 7A of the sound output portion 7 caused by a negative pressure in the pressure-resistant case.

Furthermore, since the battery 3A is detachable, it is also possible to use as a battery 3A a nickel hydride battery which is prohibited from use under a hermetically sealed condition. Moreover, the battery 3A can be replaced, thereby making it possible to use the radiation detector for a long period of time without replacing the entirety thereof.

Figure 15:
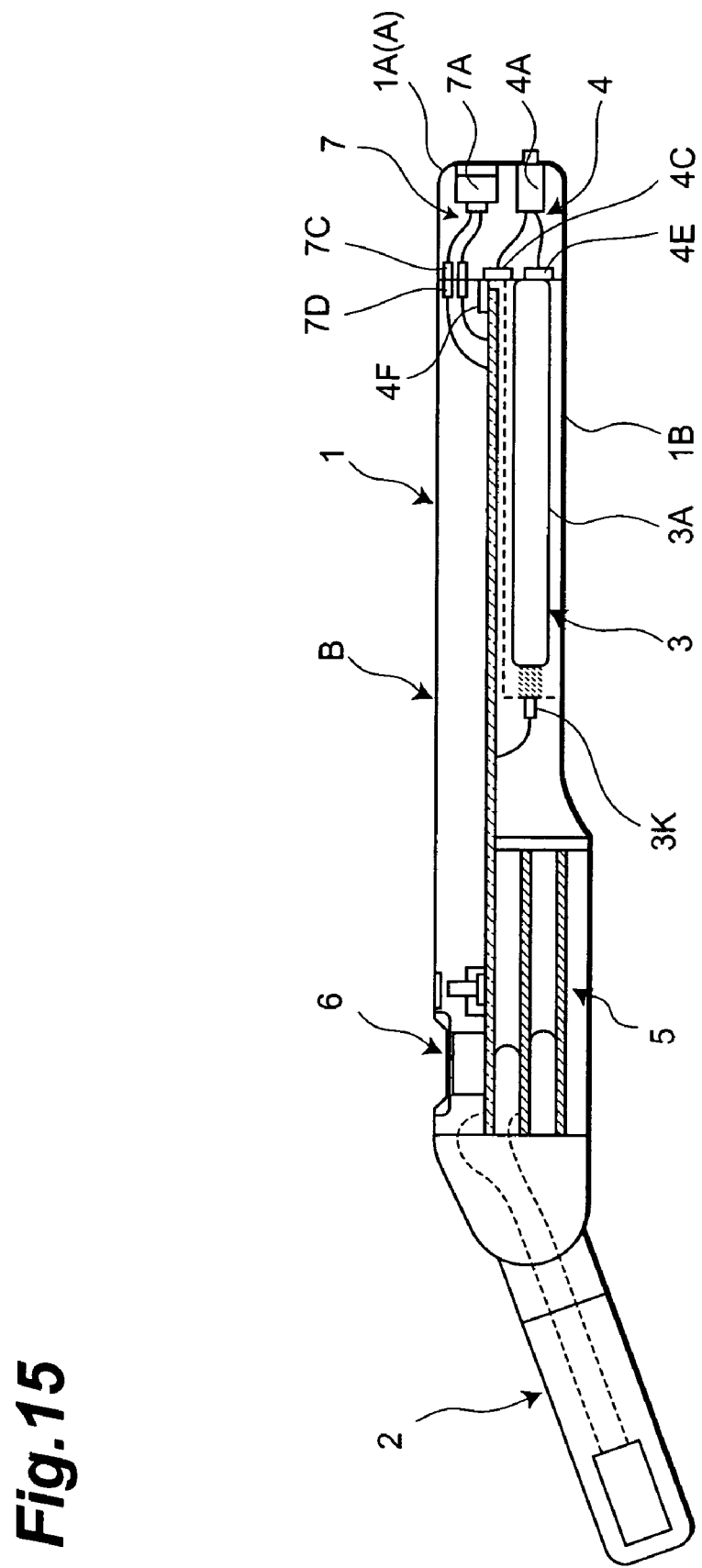
FIG. 15 is a longitudinal sectional view illustrating a schematic structure of a radiation detector according to an eighth embodiment of the present invention.
Figure 16:
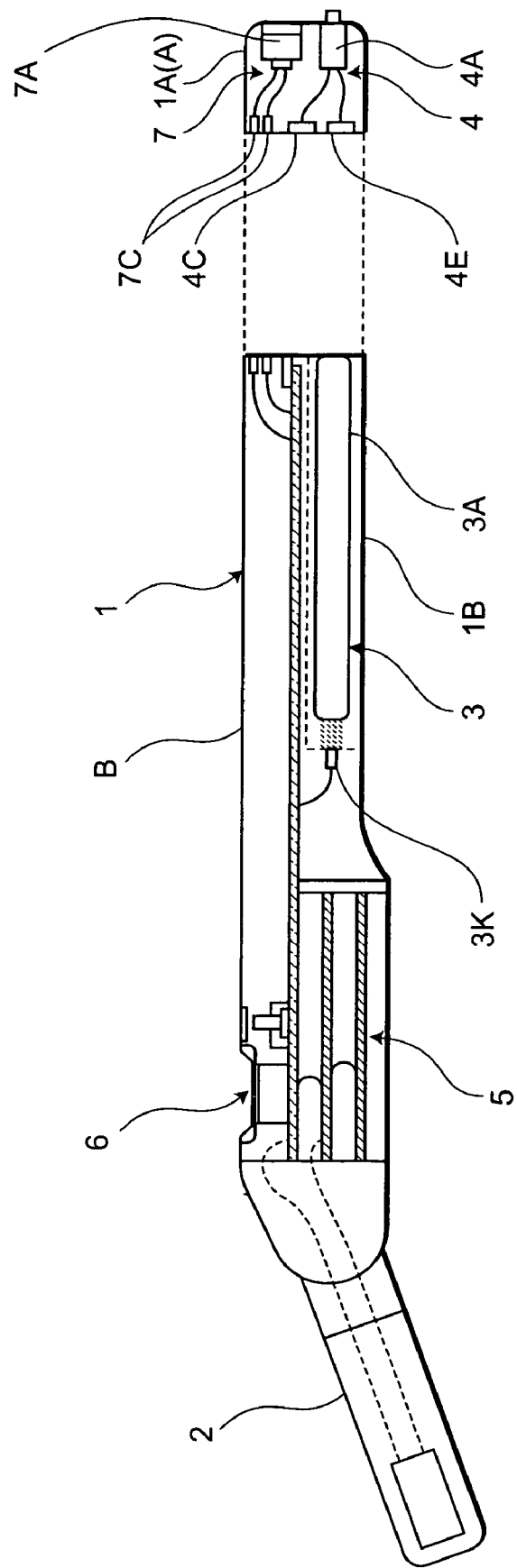
FIG. 16 is an exploded view illustrating the operation of the radiation detector shown in FIG. 15.

A radiation detector according to an eighth embodiment is configured such that the integrated component of the sound output portion 7 and the power supply switch portion 4 is detachable from the manipulation grip 1 as the main body. As shown in FIG. 15 and FIG. 16, in this radiation detector, only the grip end portion 1A that constitutes the detachable portion A of the manipulation grip 1 in the radiation detector of the fifth embodiment (refer to FIG. 9 and FIG. 10) is configured to be detachable.

In the radiation detector according to the eighth embodiment, the pair of speaker connection connectors 7C on the detachable portion A side are connected to the pair of speaker connection connectors 7D on the main body portion B side. Additionally, the one switch connection connector 4C on the detachable portion A side is connected to the other switch connection connector 4F on the main body portion B side. Furthermore, the other switch connection connector 4E is connected to the other electrode of the battery 3A. This arrangement allows the detachable portion A to be integrated with the main body portion B of the manipulation grip 1 (refer to FIG. 15).

According to the radiation detector of the eighth embodiment, it is possible to perform sterilization using a sterilizing gas such as EOG with the sound output portion 7 and the power supply switch portion 4 being removed in the manipulation grip 1 on a detachable portion A basis. This makes it possible to prevent damage to the speaker 7A of the sound output portion 7 caused by a negative pressure in the pressure-resistant case.

Furthermore, since the power supply switch portion 4 does not need to be sealed, it is possible to employ as the power supply switch 4A a mechanically selectable switch such as a dipswitch.

Figure 17:
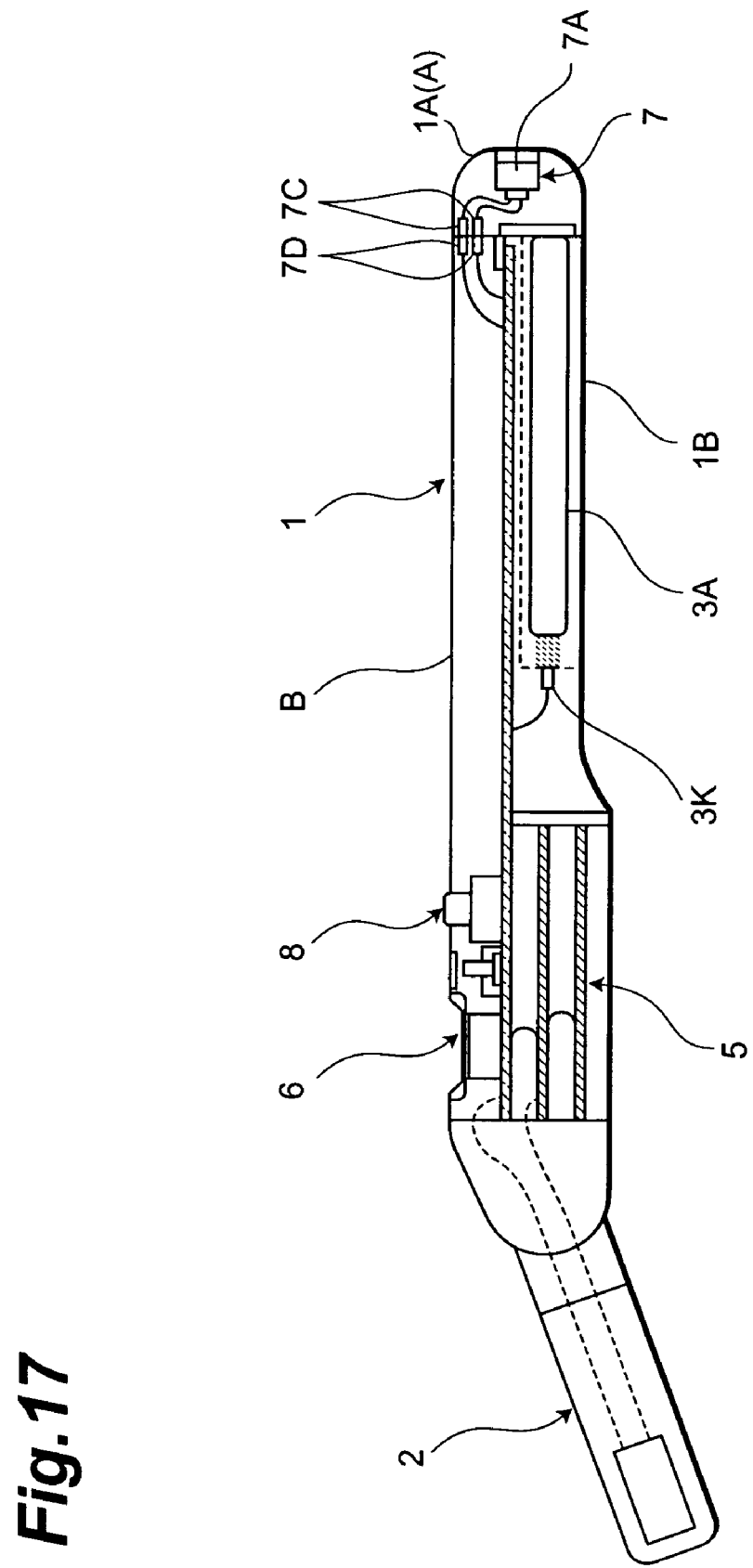
FIG. 17 is a longitudinal sectional view illustrating a schematic structure of a radiation detector according to a ninth embodiment of the present invention.
Figure 18:
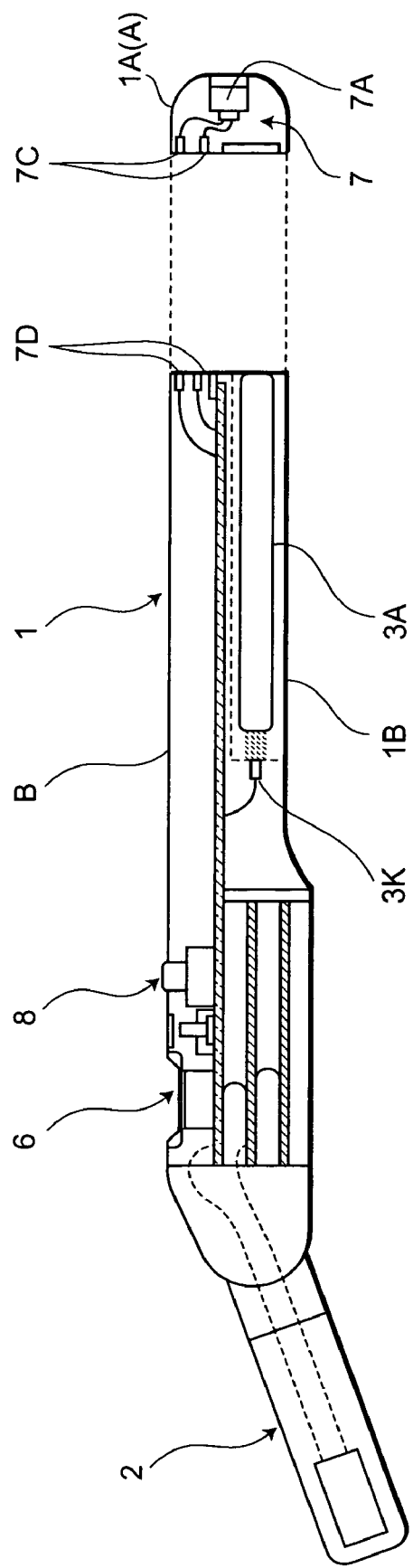
FIG. 18 is an exploded view illustrating the operation of the radiation detector shown in FIG. 17.

A radiation detector according to a ninth embodiment is configured such that the sound output portion 7 is detachable from the manipulation grip 1 as the main body. As shown in FIG. 17 and FIG. 18, in this radiation detector, only the grip end portion 1A that constitutes the detachable portion A of the manipulation grip 1 in the radiation detector of the seventh embodiment (refer to FIG. 13 and FIG. 14) is configured to be detachable.

In the radiation detector according to the ninth embodiment, the pair of speaker connection connectors 7C on the detachable portion A side are connected to the pair of speaker connection connectors 7D on the main body portion B side. This arrangement allows the detachable portion A to be integrated with the main body portion B of the manipulation grip 1 (refer to FIG. 17).

According to the radiation detector of the ninth embodiment, it is possible to perform sterilization using a sterilizing gas such as EOG with the sound output portion 7 being removed in the manipulation grip 1 on a detachable portion A basis. This makes it possible to prevent damage to the speaker 7A of the sound output portion 7 caused by a negative pressure in the pressure-resistant case.

Figure 19:
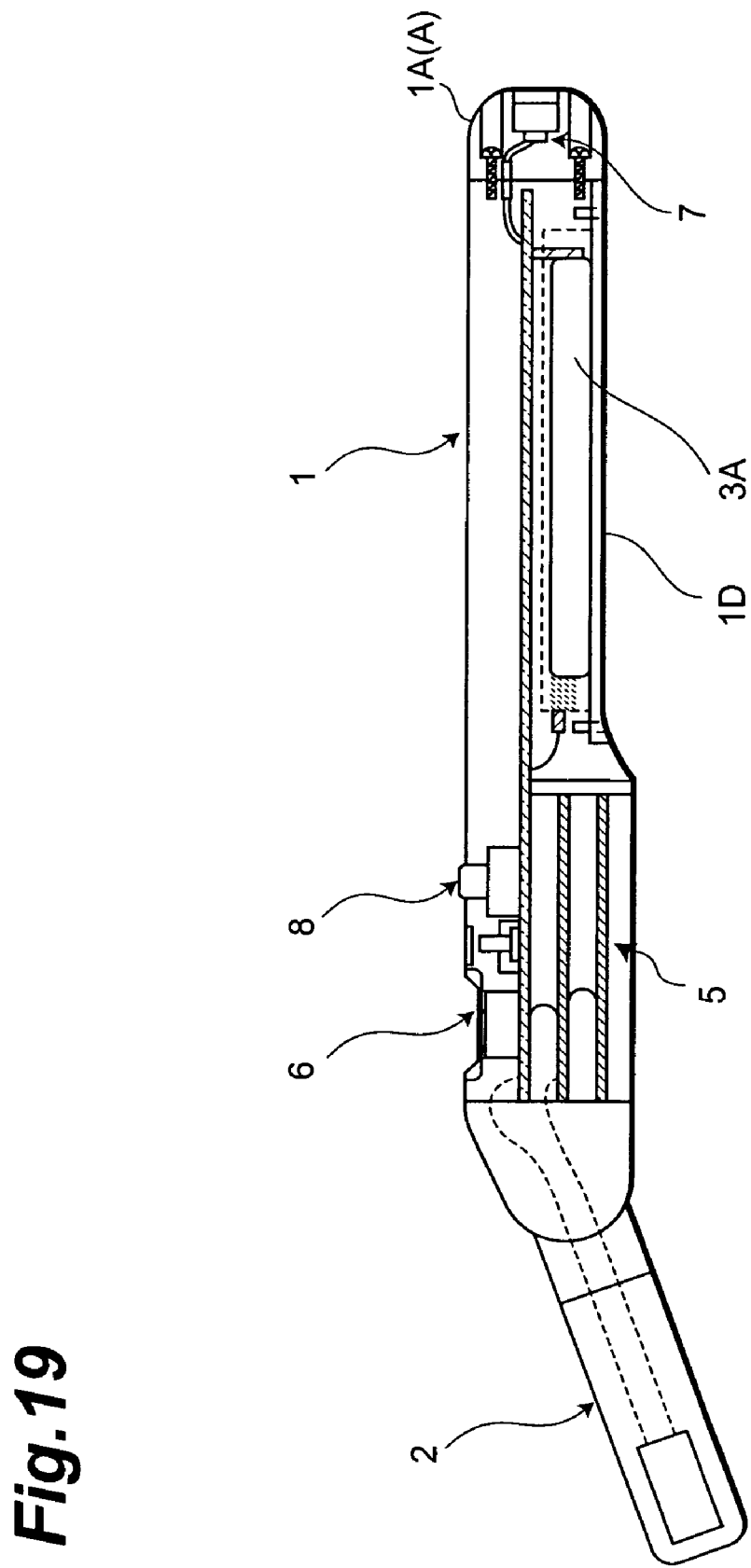
FIG. 19 is a longitudinal sectional view illustrating a schematic structure of a radiation detector according to a tenth embodiment of the present invention.
Figure 20:
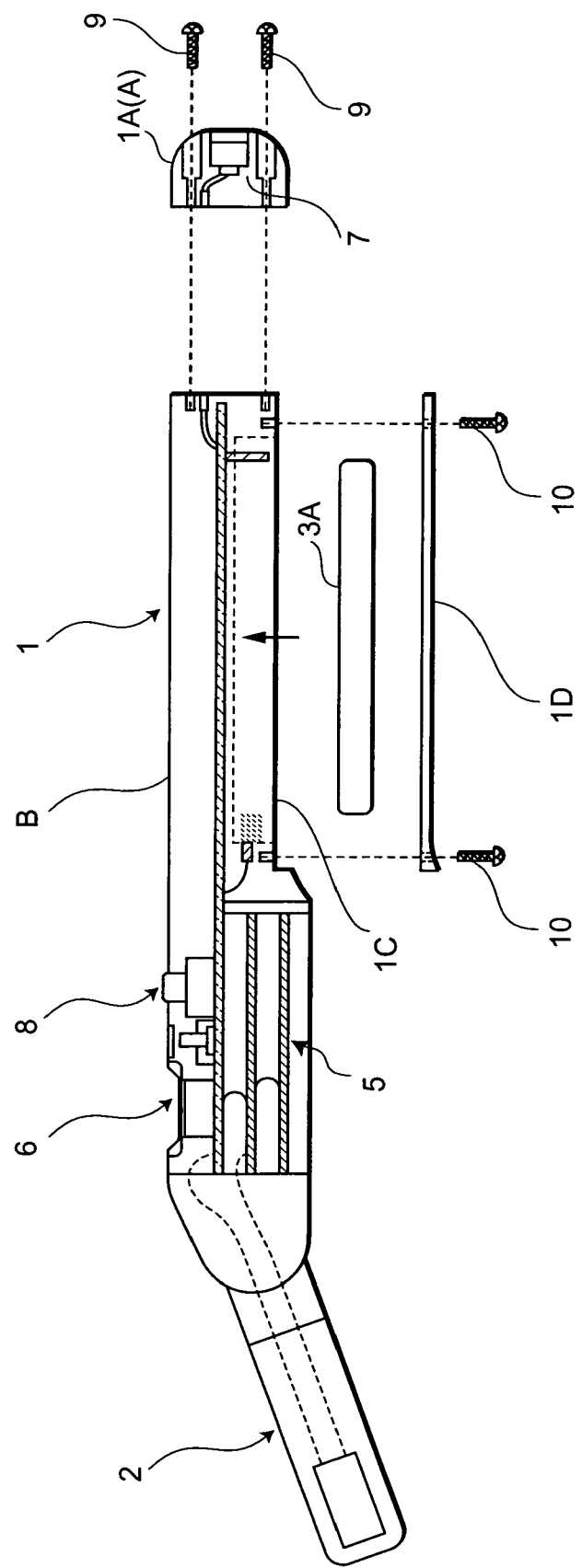
FIG. 20 is an exploded view illustrating the operation of the radiation detector shown in FIG. 19.

A radiation detector according to a tenth embodiment is configured such that the sound output portion 7 and the battery 3A are individually detachable from the manipulation grip 1 as the main body. As shown in FIG. 19 and FIG. 20, in this radiation detector, the grip end portion 1A that constitutes the detachable portion A of the manipulation grip 1 in the radiation detector of the seventh embodiment (refer to FIG. 13 and FIG. 14) is configured to be detachably screwed into the main body portion B of the manipulation grip 1. Additionally, there is formed an opening 1C which allows the battery 3A to be inserted into the lower grip body portion 1B that constitutes the main body portion B of the manipulation grip 1. A battery cover 1D which covers the opening 1C is detachably mounted to the lower grip body portion 1B using a setscrew 10.

According to the radiation detector of the tenth embodiment, it is possible to perform sterilization using a sterilizing gas such as EOG, in s state where that the sound output portion 7 is removed in the manipulation grip 1 by unscrewing a setscrew 9 on a detachable portion A basis from the main body portion B, and the battery cover 1D is also removed from the lower grip body portion 1B of the lead wire 3B by unscrewing the setscrew 10 to take out the battery 3A.

This makes it possible to prevent damage to the speaker 7A of the sound output portion 7 caused by a negative pressure in the pressure-resistant case. Furthermore, since the battery 3A is detachable, it is also possible to use as a battery 3A a nickel hydride battery which is prohibited from use under a hermetically sealed condition. Moreover, the battery 3A can be replaced, thereby making it possible to use the radiation detector for a long period of time without replacing the entirety thereof.

Figure 21:
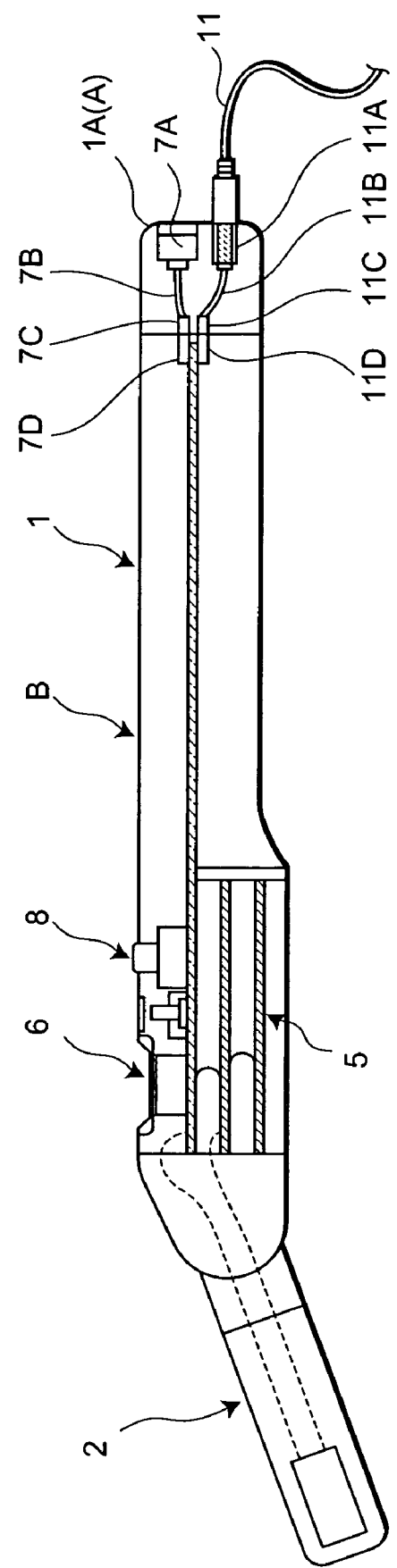
FIG. 21 is a longitudinal sectional view illustrating a schematic structure of a radiation detector according to an eleventh embodiment of the present invention.
Figure 22:
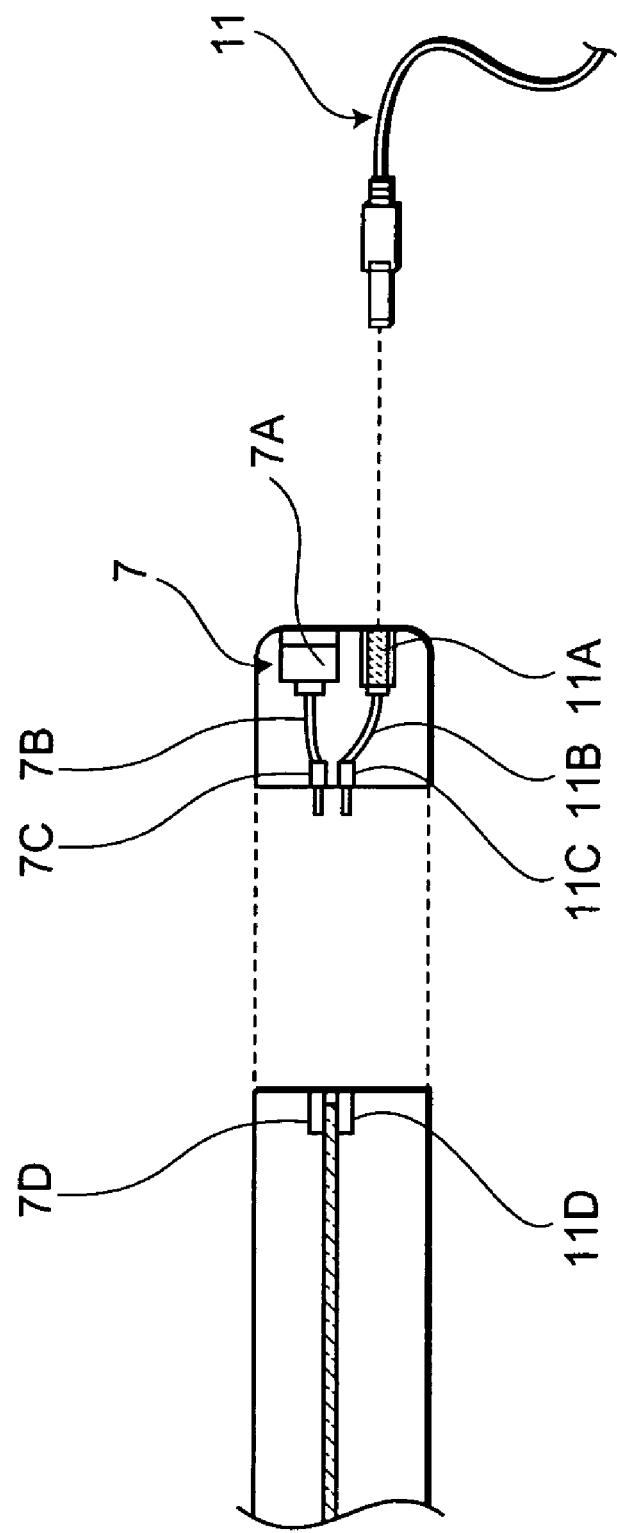
FIG. 22 is an exploded view illustrating the operation of the radiation detector shown in FIG. 21.

A radiation detector according to an eleventh embodiment is configured such that the sound output portion 7 is detachable from the manipulation grip 1 as the main body. As shown in FIG. 21 and FIG. 22, with this radiation detector, the grip end portion 1A that constitutes the detachable portion A of the manipulation grip 1 in the radiation detector of the ninth embodiment (refer to FIG. 17 and FIG. 18) is provided with an external power supply connection connector 11A, to which an external power supply cable 11 is detachably connected. And to the external power supply connection connector 11A, a power supply portion connection connector 11C is connected via a lead wire 11B. Additionally, the battery 3A is not required.

The power supply portion connection connector 11C is provided on the front end face of the grip end portion 1A. Correspondingly, a power supply portion connection connector 11D that is connected to the control portion 5 via the power supply switch portion 8 is provided on the face that is jointed to the front end face of the grip end portion 1A in the main body portion B of the manipulation grip 1.

In the radiation detector according to the eleventh embodiment, the pair of speaker connection connectors 7C on the detachable portion A side are connected to the pair of speaker connection connectors 7D on the main body portion B side. Additionally, the power supply portion connection connector 11C on the detachable portion A side is detachably connected to the power supply portion connection connector 11D on the main body portion B side such that the pin and the socket click detachably into place. This arrangement allows the detachable portion A to be integrated with the main body portion B of the manipulation grip 1 (refer to FIG. 21).

According to the radiation detector of the eleventh embodiment, it is possible to perform sterilization using a sterilizing gas such as EOG with the sound output portion 7 being removed in the manipulation grip 1 on a detachable portion A basis. This makes it possible to prevent damage to the speaker 7A of the sound output portion 7 caused by a negative pressure in the pressure-resistant case.

Furthermore, since an external power supply is used in place of the battery 3A, it is possible to use the radiation detector for a long period of time without replacement.

Figure 23:
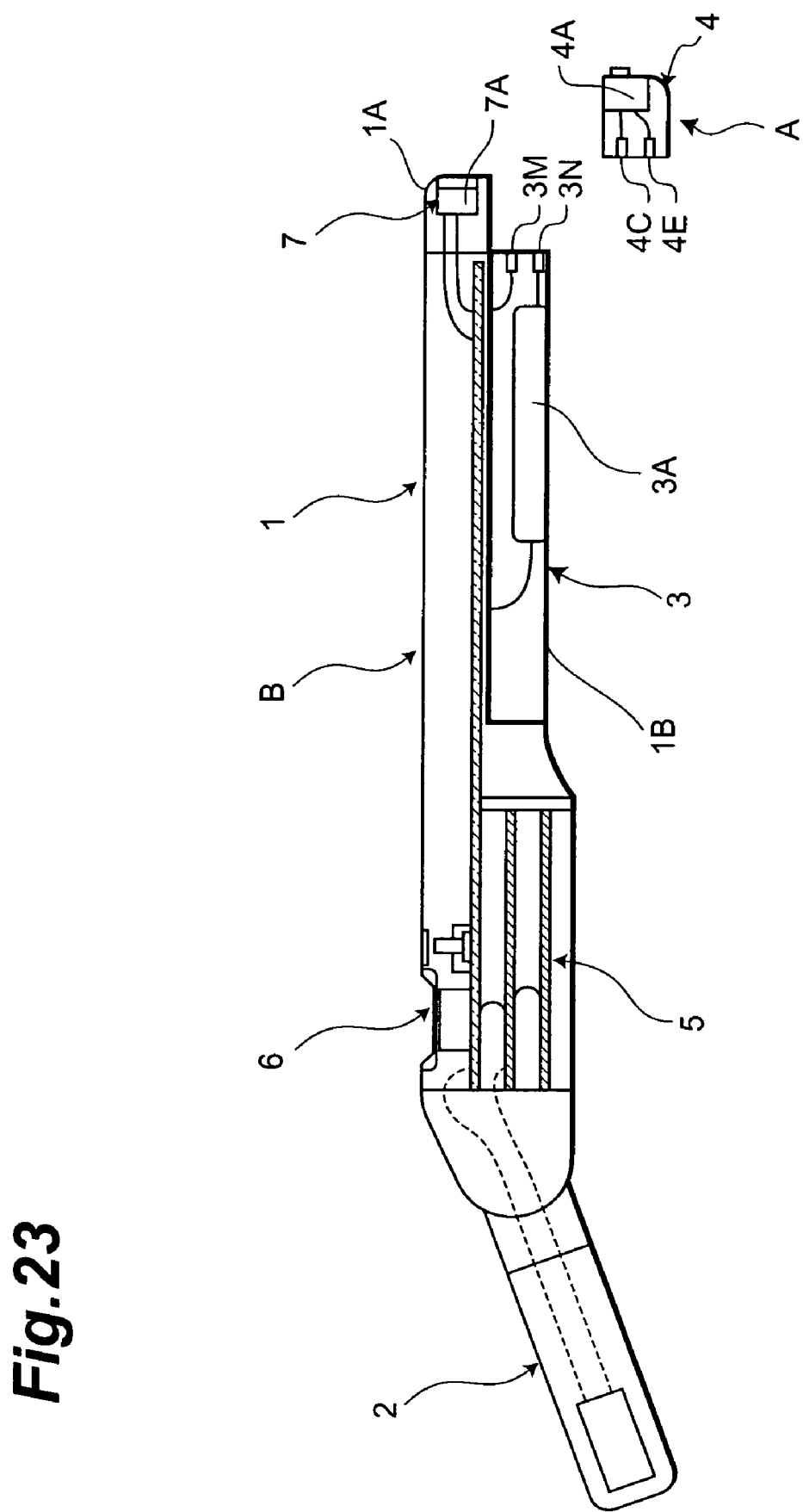
FIG. 23 is a longitudinal sectional view illustrating a schematic structure of a radiation detector according to a twelfth embodiment of the present invention.

A radiation detector according to a twelfth embodiment is configured such that the power supply switch portion 4 is detachable from the manipulation grip 1 as the main body. As shown in FIG. 23, in this radiation detector, a modification is made to the detachable portion A in the radiation detector of the eighth embodiment (refer to FIG. 15 and FIG. 16). That is, the upper portion of the grip end portion 1A accommodating the sound output portion 7 is integrated with the proximal end portion of the manipulation grip 1 as the main body portion B. Thus, only the lower portion of the grip end portion 1A accommodating the power supply switch portion 4 serves as the detachable portion A. The lower portion of the grip end portion 1A serving as the detachable portion A is jointed to the end face of the lower grip body portion 1B, on which power supply portion connection connectors 3M and 3N connected to both the electrodes of the battery 3A in the power supply portion 3 are provided vertically side by side.

In the radiation detector according to the twelfth embodiment, the switch connection connectors 4C and 4E on the lower portion side of the grip end portion 1A serving as the detachable portion A are connected to the power supply portion connection connectors 3M and 3N, respectively. Here, the power supply portion connection connectors 3M and 3N are on the side of the lower grip body portion 1B serving as the main body portion B. This arrangement allows the detachable portion A to be integrated with the main body portion B of the manipulation grip 1.

According to the radiation detector of the twelfth embodiment, it is possible to perform sterilization using a sterilizing gas such as EOG with the power supply switch portion 4 on the detachable portion A side being removed from the lower grip body portion 1B on the main body portion B side. This makes it possible to prevent the sterilizing gas such as EOG from intruding into the main body portion B through a gap in the power supply switch 4A due to a negative pressure in the pressure-resistant case.

Figure 24:
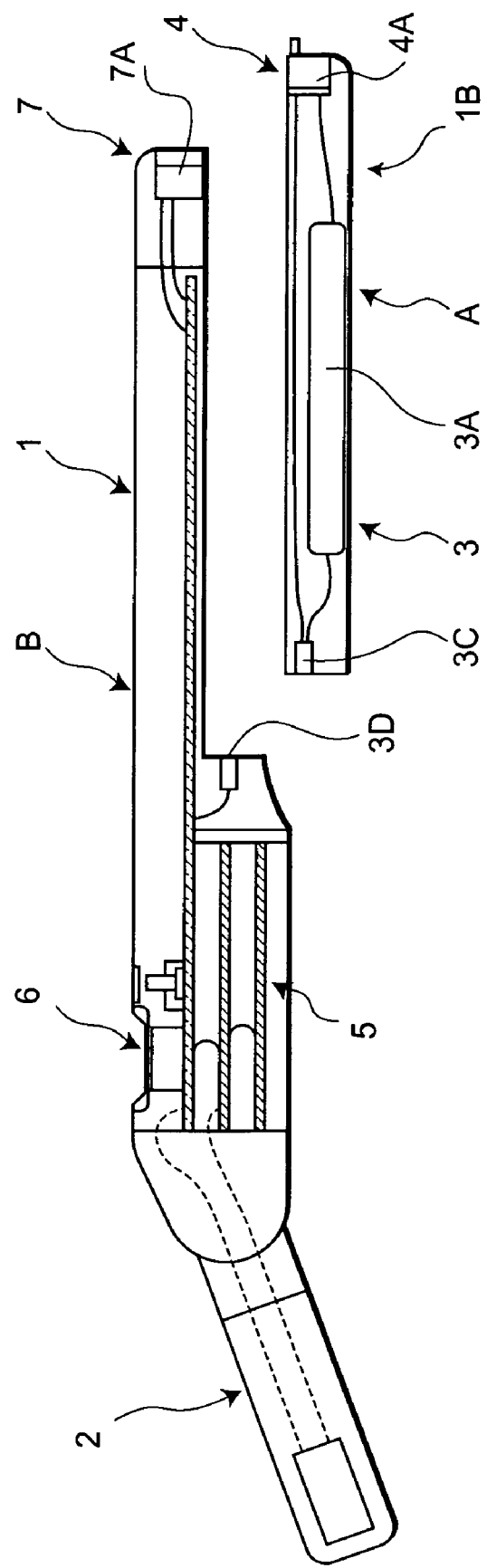
FIG. 24 is an exploded longitudinal sectional view illustrating a schematic structure of a radiation detector according to a thirteenth embodiment of the present invention.
Figure 25:
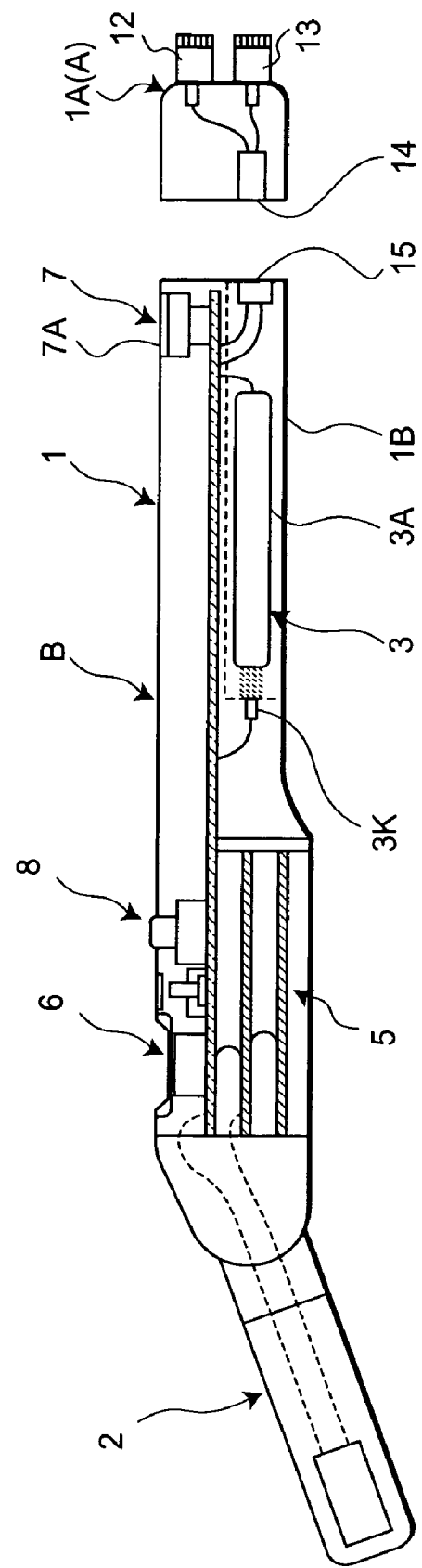
FIG. 25 is an exploded longitudinal sectional view illustrating a schematic structure of a radiation detector according to a fourteenth embodiment of the present invention.

A radiation detector according to a thirteenth embodiment is configured such that the integrated component of the power supply switch portion 4 and the power supply portion 3 is detachable from the manipulation grip 1 as the main body. As shown in FIG. 24, in this radiation detector, a modification is made to the detachable portion A in the radiation detector according to the first embodiment (refer to FIG. 1 and FIG. 2). That is, the upper portion of the grip end portion 1A accommodating the sound output portion 7 is integrated with the proximal end portion of the manipulation grip 1 as the main body portion B. The lower grip body portion 1B accommodating the power supply portion 3 is integrated with the lower portion of the grip end portion 1A accommodating the power supply switch portion 4 into the detachable portion A.

In the radiation detector according to the thirteenth embodiment, the power supply portion connection connector 3C on the detachable portion A side is connected to the power supply portion connection connector 3D on the main body portion B side. This arrangement allows the detachable portion A to be integrated with the main body portion B of the manipulation grip 1.

According to the radiation detector of the thirteenth embodiment, it is possible to perform sterilization using a sterilizing gas such as EOG with the power supply switch portion 4 and the power supply portion 3 being removed in the manipulation grip 1 on a detachable portion A basis. This makes it possible to prevent the sterilizing gas such as EOG from intruding into the main body portion B through a gap in the power supply switch 4A due to a negative pressure in the pressure-resistant case.

Furthermore, since the power supply portion 3 does not need to be sealed, it is possible to use as a battery 3A a nickel hydride battery which is prohibited from use under a hermetically sealed condition. Moreover, since the power supply portion 3 including the battery 3A can be replaced on a detachable portion A basis, it is possible to use the radiation detector for a long period of time without replacing the entirety thereof.

A radiation detector according to a fourteenth embodiment includes a detection sensitivity variable portion capable of varying the detection sensitivity of the radiation detecting probe 2 (the radiation detecting portion) and a display variable portion capable of varying a sound display from the sound output portion 7 for displaying the radiation intensity detected by the radiation detecting probe 2 (the radiation detecting portion). The display variable portion is also capable of varying an image display from the liquid crystal display portion 6. The radiation detector is configured such that detection sensitivity variable portion and the display variable portion are detachable from the manipulation grip 1 as the main body. This radiation detector is configured, similar to the radiation detector of the eighth embodiment (refer to FIG. 15 and FIG. 16), such that only the grip end portion 1A of the manipulation grip 1 serves as the detachable portion A. However, in this arrangement, the power supply switch portion 8 as a substitute for the power supply switch portion 4 (refer to FIG. 16) is provided behind the liquid crystal display portion 6 in the main body portion B of the manipulation grip 1. Also, the sound output portion 7 is provided on an end portion of the manipulation grip 1 to which the grip end portion 1A is jointed.

Here, the grip end portion 1A serving as the detachable portion A is additionally provided with a detection sensitivity variable knob 12 that constitutes the detection sensitivity variable portion capable of varying the detection sensitivity of the radiation detecting probe 2 (the radiation detecting portion), and a volume variable knob 13 that constitutes the display variable portion capable of varying the volume of the speaker 7A for displaying the detected radiation intensity. A connection connector 14 that is connected to the detection sensitivity variable knob 12 and the volume variable knob 13 is provided on the front end face of the grip end portion 1A. A connection connector 15 that is detachably connected to the connection connector 14 is provided on the rear end face of the lower grip body portion 1B of the manipulation grip 1 serving as the main body portion B.

In the radiation detector according to the fourteenth embodiment, the connection connector 14 on the detachable portion A side is connected to the connection connector 15 on the main body portion B side. This arrangement allows the detachable portion A to be integrated with the main body portion B of the manipulation grip 1.

According to the radiation detector of the fourteenth embodiment, it is possible to perform sterilization using a sterilizing gas such as EOG, in a state where, the detection sensitivity variable control 12 and the volume variable control 13 are removed on a grip end portion 1A basis, the grip end portion 1A serving as the detachable portion A of the manipulation grip 1. This makes it possible to prevent the sterilizing gas such as EOG from intruding into the main body portion B through a gap in the detection sensitivity variable control 12 or the volume variable control 13 due to a negative pressure in the pressure-resistant case.

The radiation detector according to the above-mentioned embodiments is designed as a medical surgical probe; however, the use of the radiation detector of the present invention is not limited thereto but may also be employed in a wide range of other applications.

INDUSTRIAL APPLICABILITY

For example, the present invention can be applied to the detection of the developing location of cancer using a radiopharmaceutical.

The invention claimed is:

1. A radiation detector with a manipulation grip, comprising:
   a main body portion including:
      a radiation detecting portion having a radiation detection probe disposed at a first end of the manipulation grip for detecting a radiation intensity, a radiation detection element being provided in the radiation detection probe and being a semiconductor element for generating a voltage pulse signal having a pulse height value corresponding to the energy of the radiation photon;
      a liquid crystal display portion being disposed near the first end of the manipulation grip,
      a control unit provided near the first end of the manipulator grip, for processing the voltage pulse signal from the radiation detection element, and
      a power supply switch electrically connected to the control unit and provided near the first end of the manipulation grip for switching over power supply to the control;
   a detachable portion with respect to the main body portion, the detachable portion being disposed at a second end of the manipulation grip and including:
      a sound output portion having a speaker for outputting a sound according to the radiation intensity detected by the radiation detecting portion, and
      a power supply portion for supplying power at least to the radiation detecting portion, the sound output portion and the control unit.

2. The radiation detector according to claim 1, wherein the sound output portion includes a connection connector to be detachably connected to a connection connector of the main body, and is configured to be detachable from the main body via the connection connector.

3. The radiation detector according to claim 1, wherein the sound output portion is detachably screwed to the main body.

4. The radiation detector according to claim 1, wherein the sound output portion includes an engagement portion to detachably engage an engagement portion of the main body, and is configured to be detachable from the main body via the engagement portion.

5. The radiation detector according to claim 1, wherein a longitudinal direction of the radiation detection probe is inclined with respect to a longitudinal direction of the manipulation grip.

* * * * *